(12) United States Patent
McGuckin, Jr. et al.

(10) Patent No.: US 6,960,172 B2
(45) Date of Patent: Nov. 1, 2005

(54) SURGICAL BIOPSY DEVICE

(75) Inventors: James F. McGuckin, Jr., Radnor, PA (US); Peter W. J. Hinchliffe, Downington, PA (US); Stephan A. Defonzo, Wayne, PA (US)

(73) Assignee: Rex Medical, L.P., Conshohocken, PA (US)

( * ) Notice: Subject to any disclaimer, the term of this patent is extended or adjusted under 35 U.S.C. 154(b) by 0 days.

(21) Appl. No.: 10/642,009

(22) Filed: Aug. 15, 2003

(65) Prior Publication Data

US 2004/0087942 A1 May 6, 2004

Related U.S. Application Data

(63) Continuation of application No. 09/844,729, filed on Apr. 27, 2001, now Pat. No. 6,626,903, which is a continuation-in-part of application No. 09/122,185, filed on Jul. 23, 1998, now Pat. No. 6,280,450.
(60) Provisional application No. 60/053,664, filed on Jul. 24, 1997.

(51) Int. Cl.⁷ .............................................. A61B 10/00
(52) U.S. Cl. ......................................... 600/564; 606/45
(58) Field of Search ........................ 600/562, 564–567; 606/41, 45, 113, 114

(56) References Cited

U.S. PATENT DOCUMENTS

| | | |
|---|---|---|
| 2,816,552 A | 12/1957 | Hoffman |
| 3,320,957 A | 5/1967 | Sokolik |
| 4,011,872 A | 3/1977 | Komiya |
| 4,503,855 A | 3/1985 | Maslanka |
| 4,611,594 A | 9/1986 | Grayhack et al. |
| 4,616,656 A | 10/1986 | Nicholson et al. |
| 4,935,027 A | 6/1990 | Yoon |
| 4,966,604 A | 10/1990 | Reiss |
| 4,976,711 A | 12/1990 | Parins et al. |
| 4,997,435 A | 3/1991 | Demeter |
| 5,078,716 A | 1/1992 | Doll |
| 5,100,423 A | 3/1992 | Fearnot |
| 5,176,128 A | 1/1993 | Andrese |
| 5,190,561 A | 3/1993 | Graber |
| 5,197,968 A | 3/1993 | Clement |
| 5,201,741 A | 4/1993 | Dulebohn |
| 5,207,675 A | 5/1993 | Canady |
| 5,221,269 A | 6/1993 | Miller et al. |
| 5,224,488 A | 7/1993 | Neuffer |
| 5,281,238 A | 1/1994 | Chin et al. |
| 5,282,484 A | 2/1994 | Reger |

(Continued)

FOREIGN PATENT DOCUMENTS

| | | |
|---|---|---|
| SU | 1683701 | 10/1991 |
| WO | WO 8905608 | 6/1989 |
| WO | WO 9502370 | 1/1995 |
| WO | WO 9944506 | 9/1999 |
| WO | 002082230 | 1/2000 |
| WO | WO 0012009 | 3/2000 |
| WO | WO 0030531 | 6/2000 |
| WO | WO 0033743 | 6/2000 |
| WO | WO 0044295 | 8/2000 |
| WO | WO 0074561 | 12/2000 |
| WO | WO 0105320 | 1/2001 |
| WO | WO 0128445 | 4/2001 |
| WO | WO 0128446 | 4/2001 |

*Primary Examiner*—Rosiland Rollins
(74) *Attorney, Agent, or Firm*—Neil D. Gershon

(57) ABSTRACT

A surgical biopsy apparatus for cutting tissue comprising a housing having a longitudinal axis, first and second members movable from a retracted position to an extended position with respect to the housing, a third member slidably positioned and extendable with respect to the first member, a fourth member slidably positioned and extendable with respect to the second member, and an electrocautery cutting wire slidable with respect to the third and fourth members to surround a region of tissue positioned between the third and fourth members to cut the tissue.

15 Claims, 30 Drawing Sheets

U.S. PATENT DOCUMENTS

| | | |
|---|---|---|
| 5,318,576 A | 6/1994 | Plassche, Jr. et al. |
| 5,353,804 A | 10/1994 | Kornberg et al. |
| 5,370,647 A | 12/1994 | Graber et al. |
| 5,376,100 A | 12/1994 | Lefebvre |
| 5,397,320 A | 3/1995 | Essig et al. |
| 5,417,697 A | 5/1995 | Wilk et al. |
| 5,437,665 A | 8/1995 | Munro |
| 5,439,474 A | 8/1995 | Li |
| 5,486,183 A | 1/1996 | Middleman et al. |
| 5,496,330 A | 3/1996 | Bates et al. |
| 5,514,153 A | 5/1996 | Bonutti |
| 5,524,633 A | 6/1996 | Heaven et al. |
| 5,573,008 A | 11/1996 | Robinson et al. |
| 5,632,746 A | 5/1997 | Middleman et al. |
| 5,649,547 A | 7/1997 | Ritchart et al. |
| 5,653,684 A | 8/1997 | Laptweicz et al. |
| 5,709,697 A | 1/1998 | Ratcliff et al. |
| 5,735,289 A | 4/1998 | Pfeffer et al. |
| 5,746,747 A | 5/1998 | McKeating |
| 5,759,187 A | 6/1998 | Nakao et al. |
| 5,794,626 A | 8/1998 | Kieturakis |
| 5,810,806 A | 9/1998 | Ritchart et al. |
| 5,820,629 A | 10/1998 | Cox |
| 5,836,953 A | 11/1998 | Yoon |
| 5,853,374 A | 12/1998 | Hart et al. |
| 5,871,454 A | 2/1999 | Majlessi |
| 5,879,357 A | 3/1999 | Heaton et al. |
| 5,885,278 A | 3/1999 | Fleischman |
| 5,895,361 A | 4/1999 | Turturro |
| 5,895,392 A | 4/1999 | Riek et al. |
| 5,895,417 A | 4/1999 | Pomeranz et al. |
| 5,897,567 A | 4/1999 | Ressemann et al. |
| 5,904,679 A | 5/1999 | Clayman |
| 5,947,964 A | 9/1999 | Eggers et al. |
| 5,989,266 A | 11/1999 | Foster |
| 6,007,495 A | 12/1999 | Matula |
| 6,022,362 A | 2/2000 | Lee et al. |
| 6,036,698 A | 3/2000 | Fawzi et al. |
| 6,053,876 A | 4/2000 | Fisher |
| 6,056,700 A | 5/2000 | Burney et al. |
| 6,059,734 A | 5/2000 | Yoon |
| 6,068,603 A | 5/2000 | Suzuki |
| 6,080,113 A | 6/2000 | Heneveld et al. |
| 6,080,114 A | 6/2000 | Russin |
| 6,096,053 A | 8/2000 | Bates |
| 6,106,524 A | 8/2000 | Eggers et al. |
| 6,165,137 A | 12/2000 | Milliman et al. |
| 6,171,315 B1 | 1/2001 | Chu et al. |
| 6,179,860 B1 | 1/2001 | Fulton, III et al. |
| 6,190,394 B1 | 2/2001 | Lind et al. |
| 6,216,043 B1 | 4/2001 | Swanson et al. |
| 6,221,006 B1 | 4/2001 | Dubrul et al. |
| 6,261,241 B1 | 7/2001 | Burbank et al. |
| 6,277,083 B1 | 8/2001 | Eggers et al. |
| 6,287,304 B1 | 9/2001 | Eggers et al. |
| 6,312,428 B1 | 11/2001 | Eggers et al. |
| 6,312,429 B1 | 11/2001 | Burbank et al. |
| 6,331,166 B1 | 12/2001 | Burbank et al. |
| 6,344,026 B1 | 2/2002 | Burbank et al. |
| 6,375,654 B1 | 4/2002 | McIntyre |
| 6,454,727 B1 | 9/2002 | Burbank et al. |
| 6,455,727 B1 | 9/2002 | Burbank |
| 6,471,659 B2 | 10/2002 | Eggers et al. |
| 6,471,700 B1 | 10/2002 | Burbank et al. |
| 6,517,498 B1 | 2/2003 | Burbank et al. |
| 6,530,923 B1 | 3/2003 | Dubrul et al. |
| 6,540,693 B2 | 4/2003 | Burbank et al. |
| 6,540,695 B1 | 4/2003 | Burbank et al. |
| 6,602,204 B2 | 8/2003 | Dubrul et al. |
| 6,638,234 B2 * | 10/2003 | Burbank et al. ............ 600/564 |
| 6,659,105 B2 | 12/2003 | Burbank et al. |
| 6,679,851 B2 | 1/2004 | Burbank et al. |
| 2003/0109870 A1 | 6/2003 | Lee et al. |

* cited by examiner

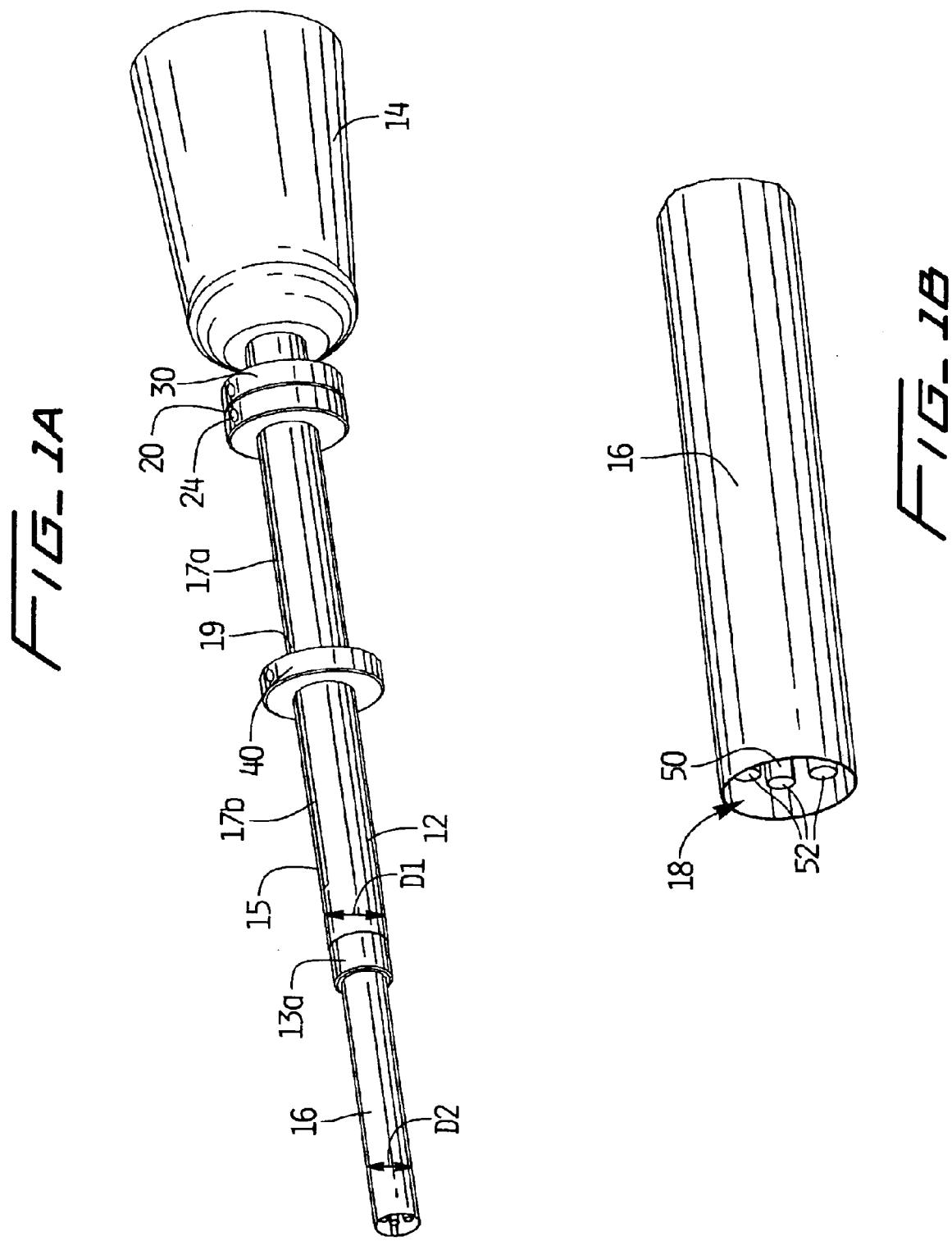

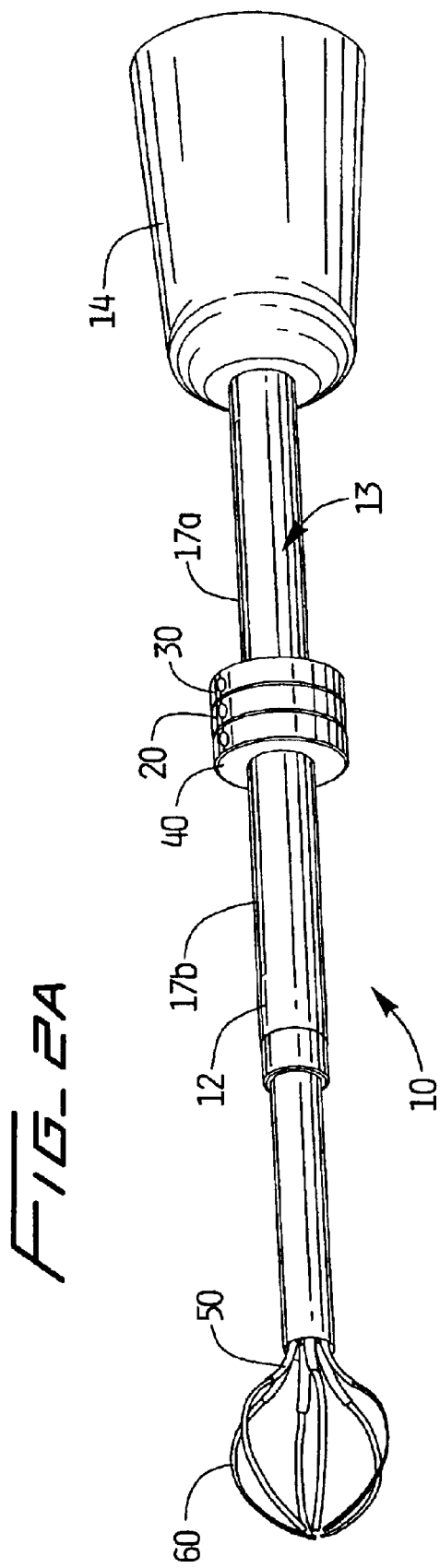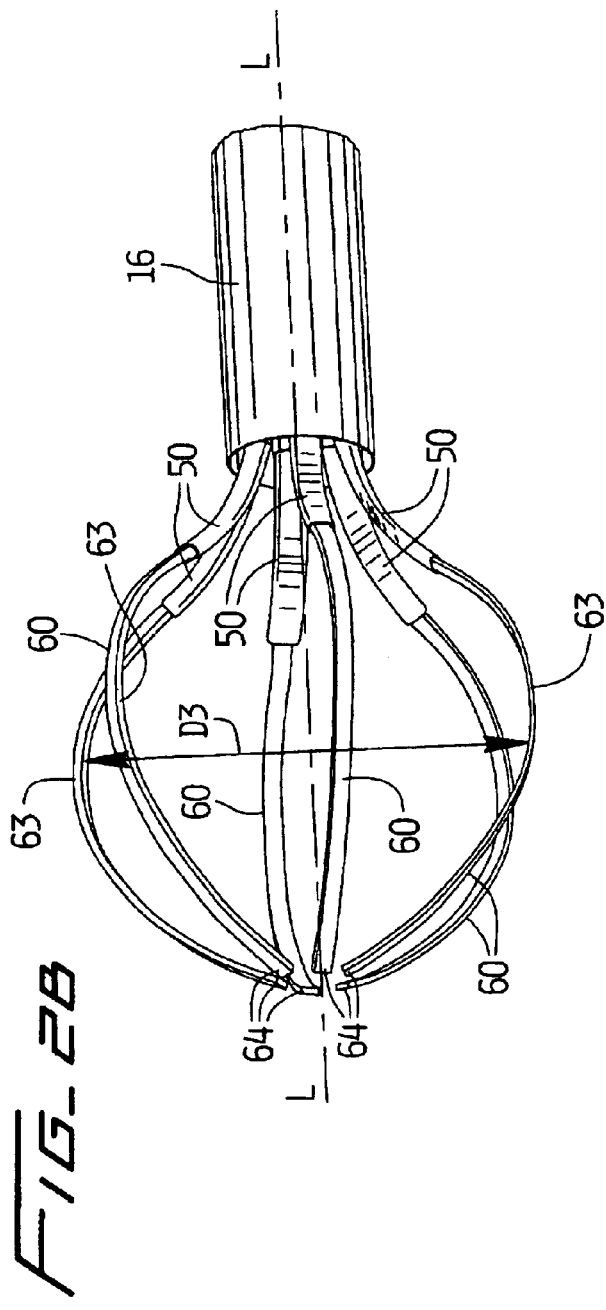
FIG. 2A
FIG. 2B

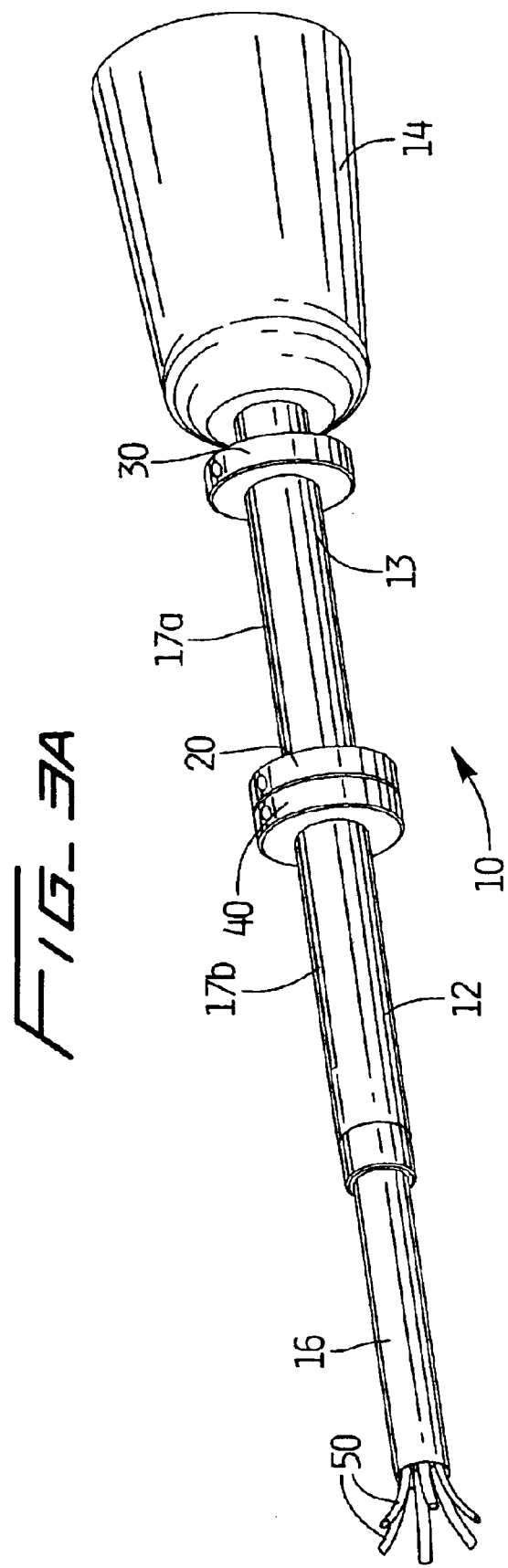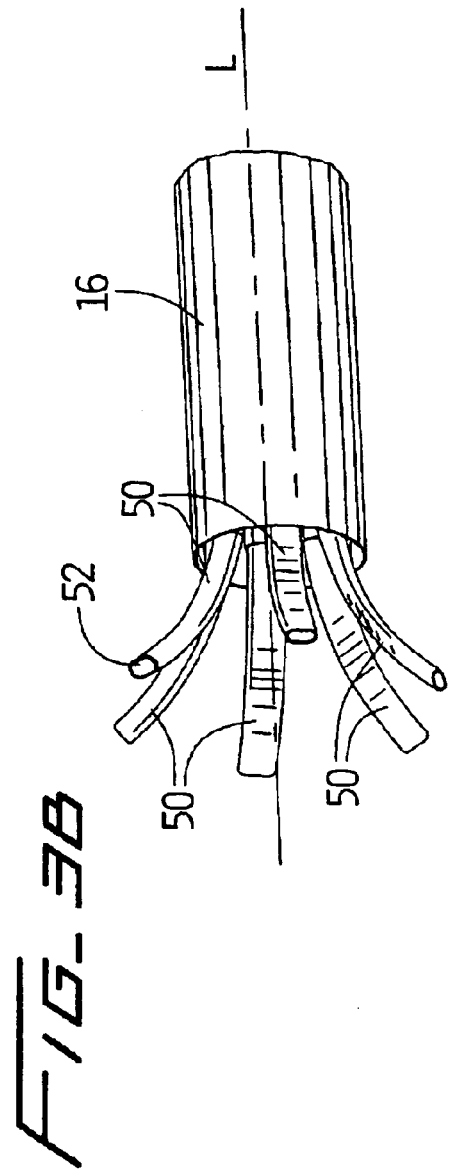

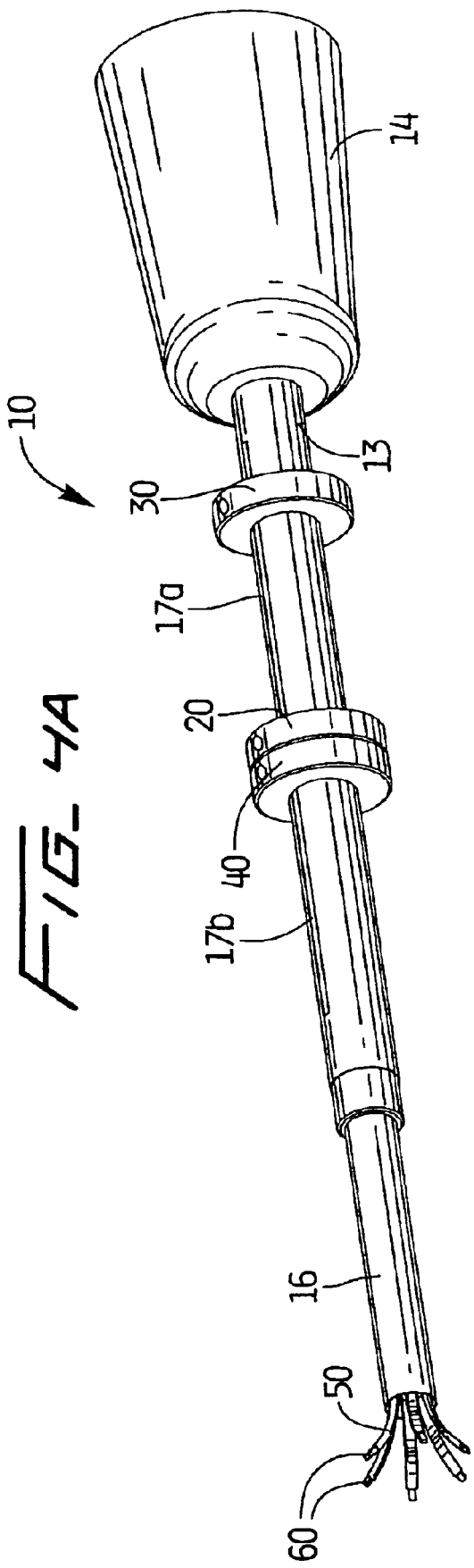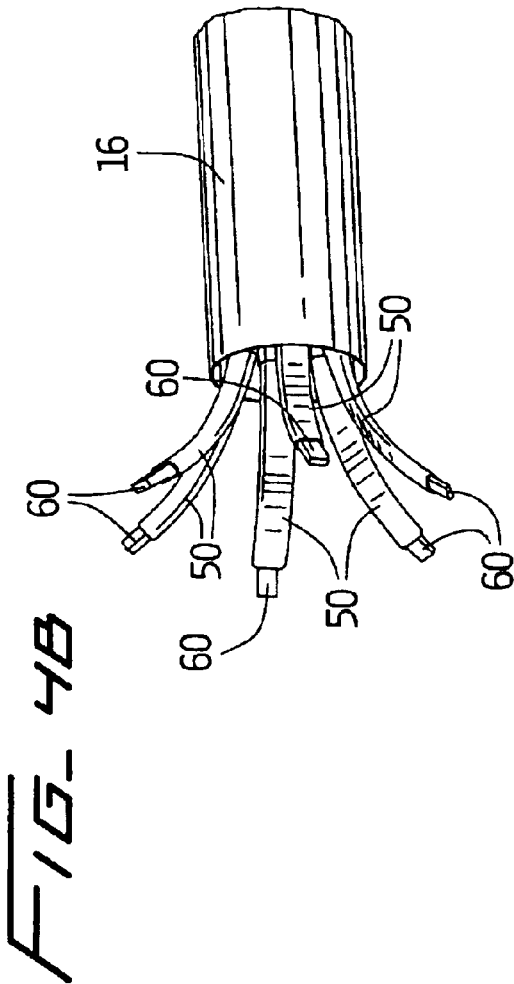

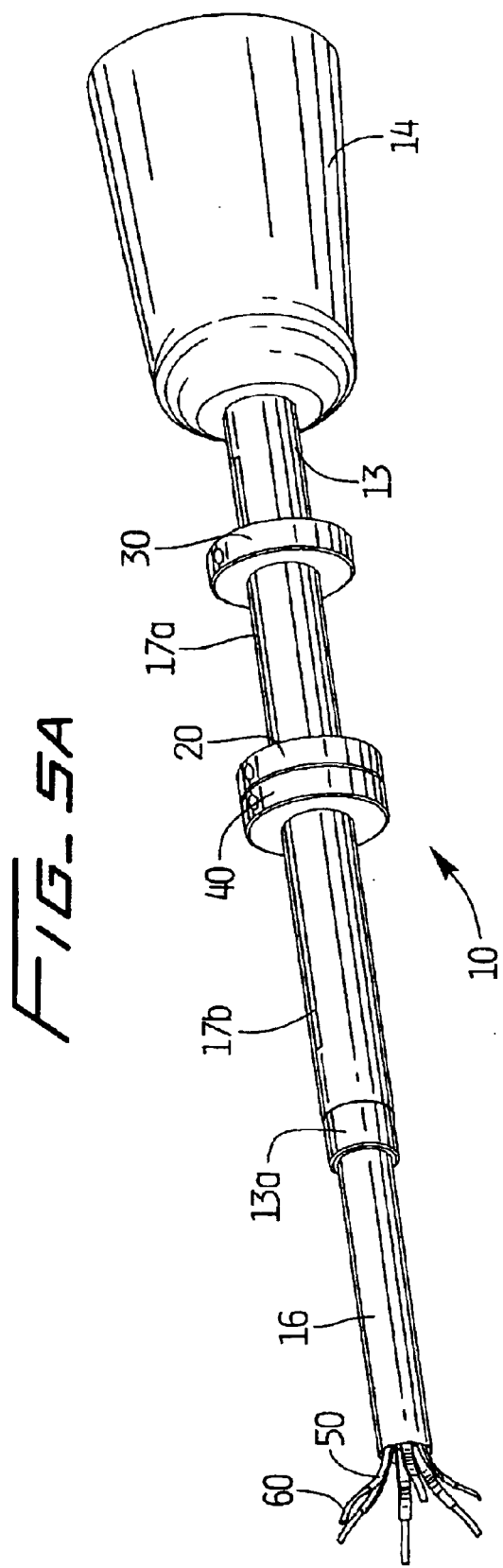
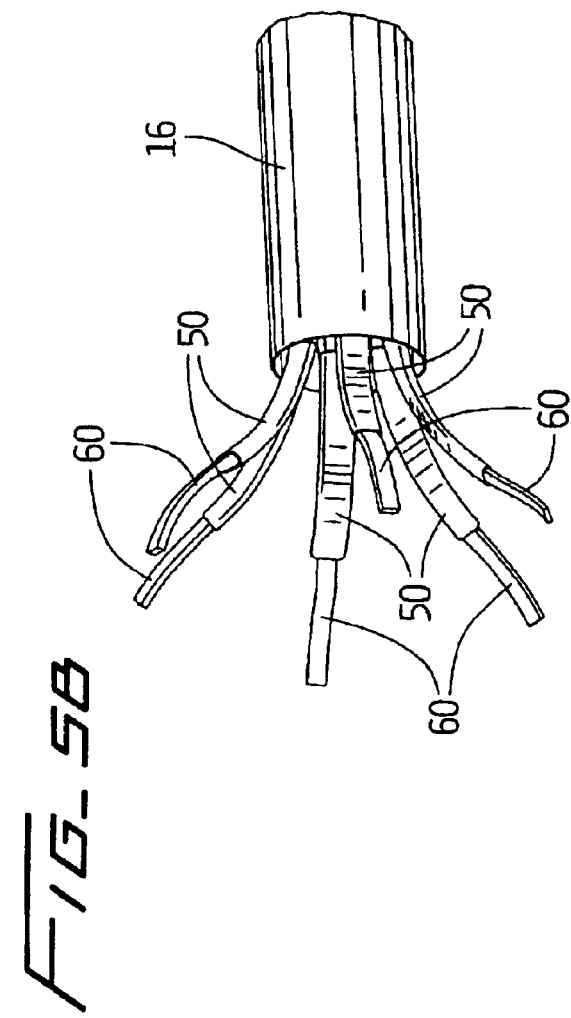
FIG. 5A
FIG. 5B

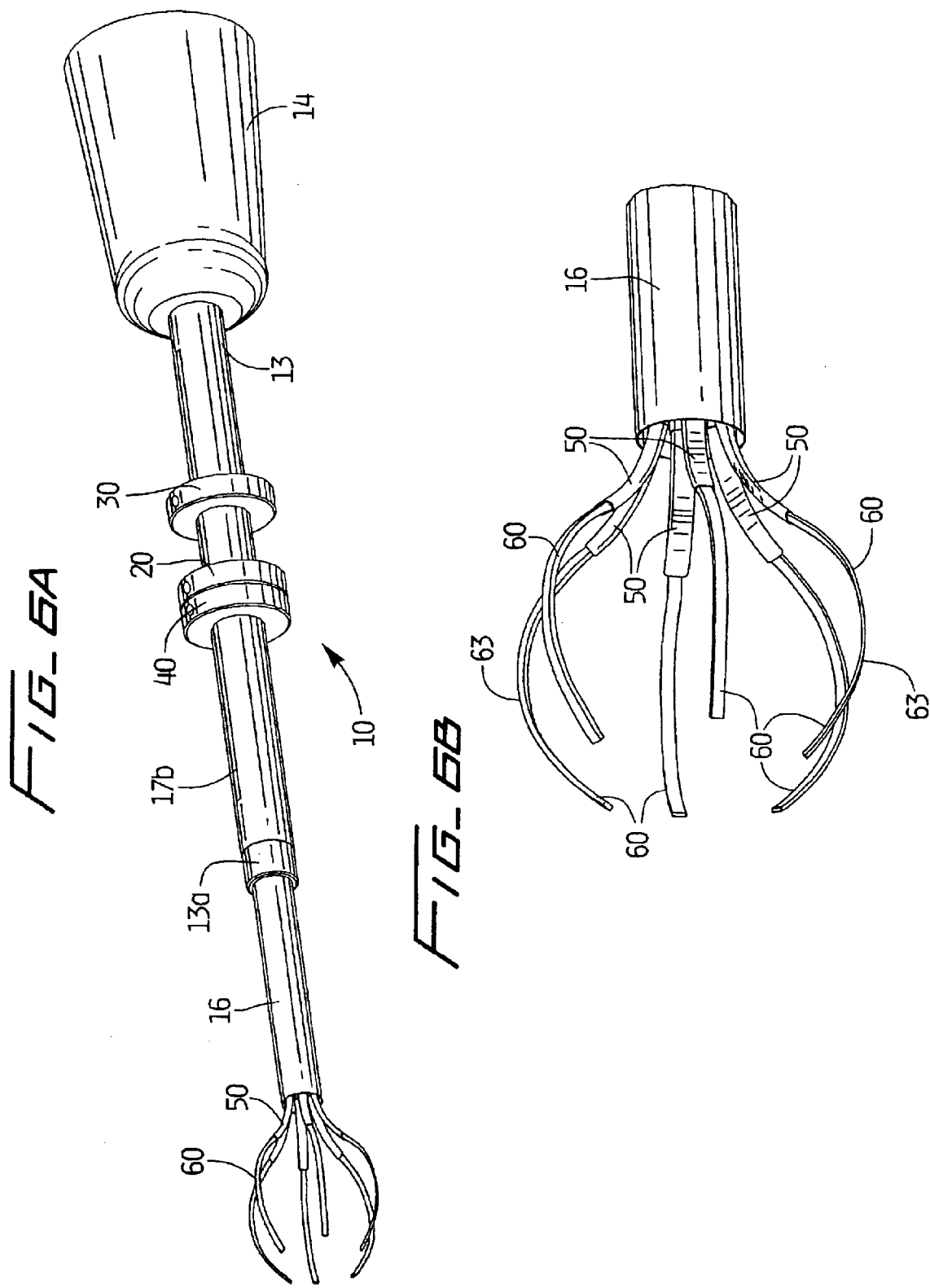

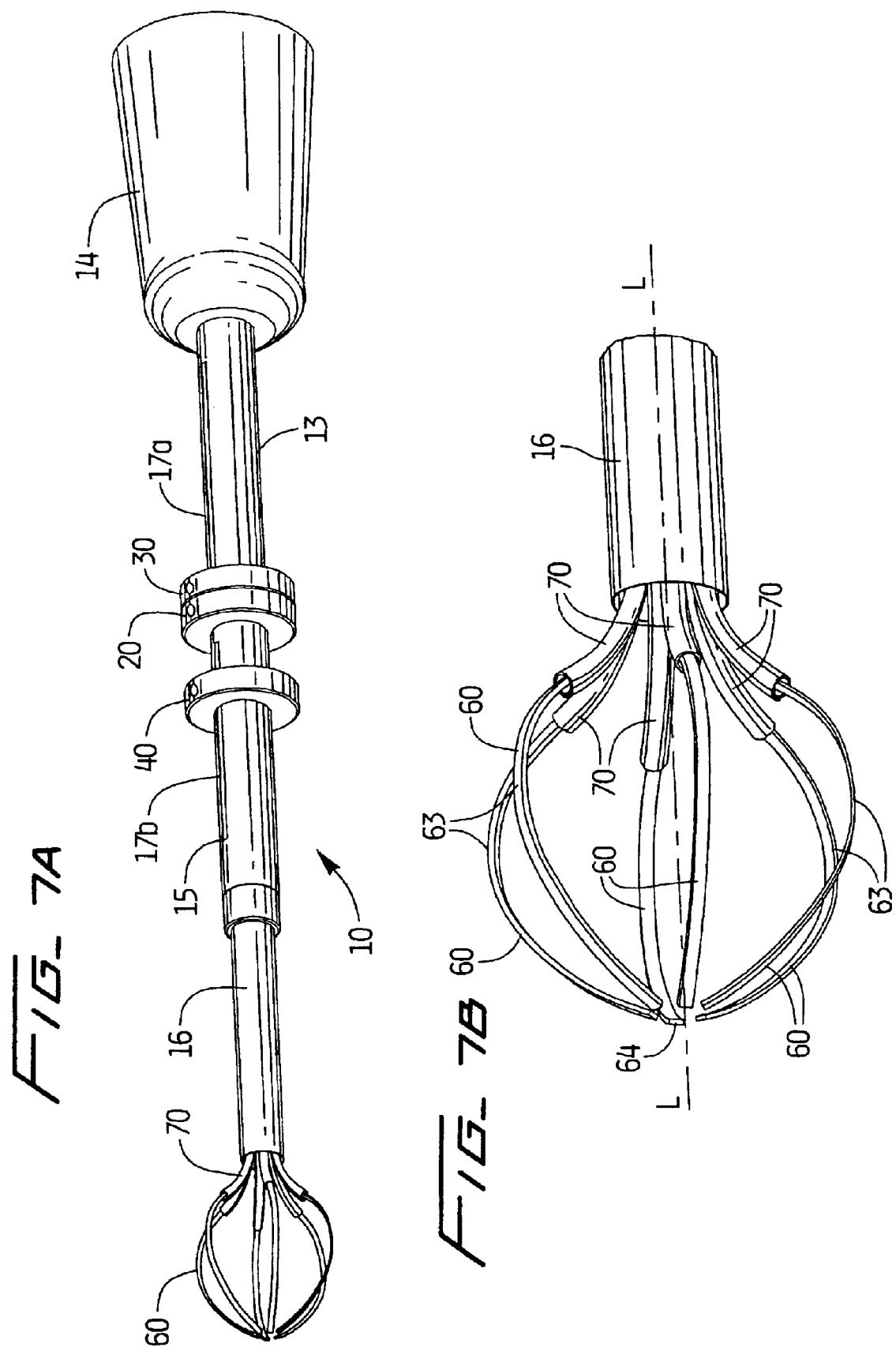

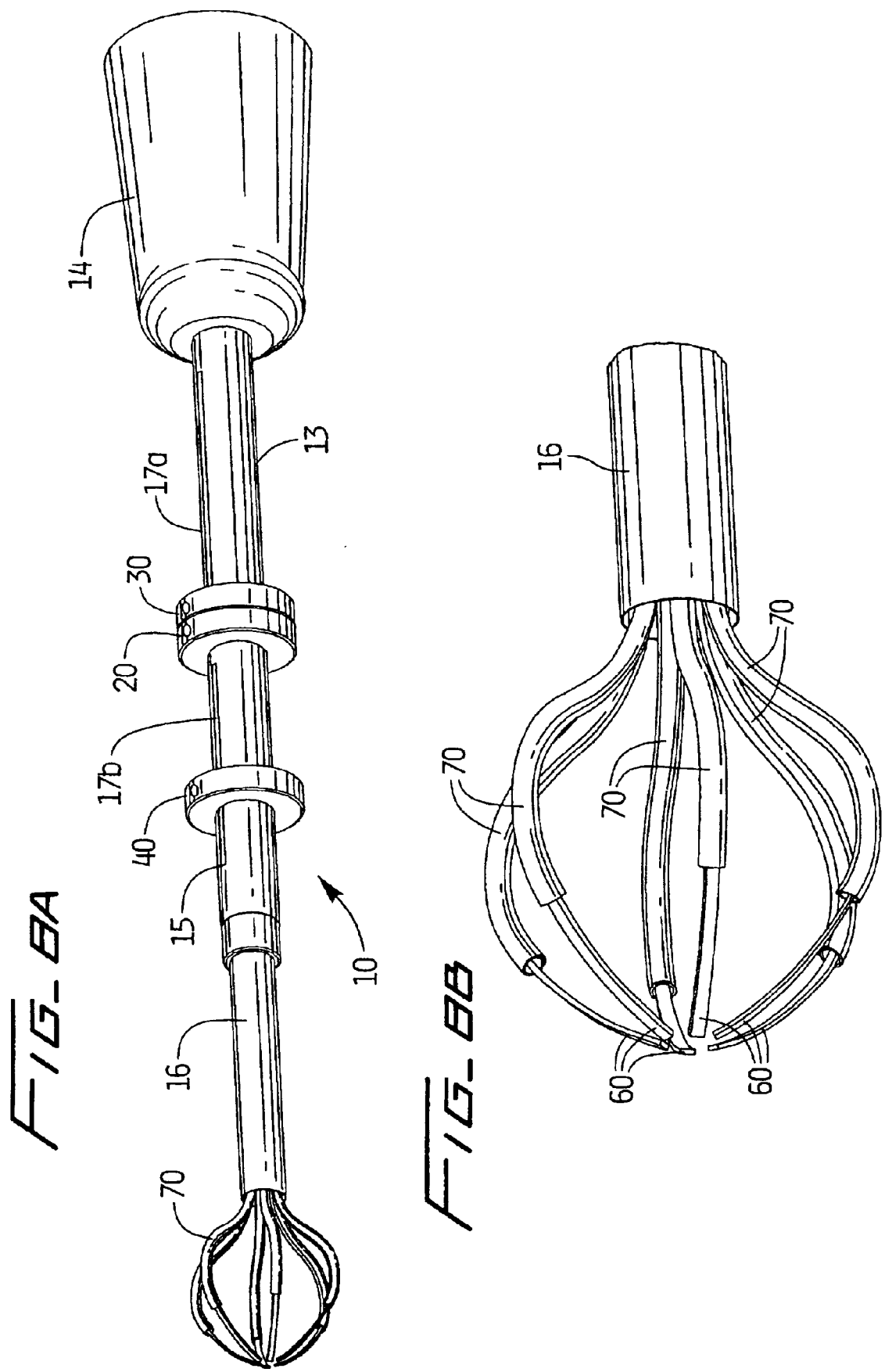

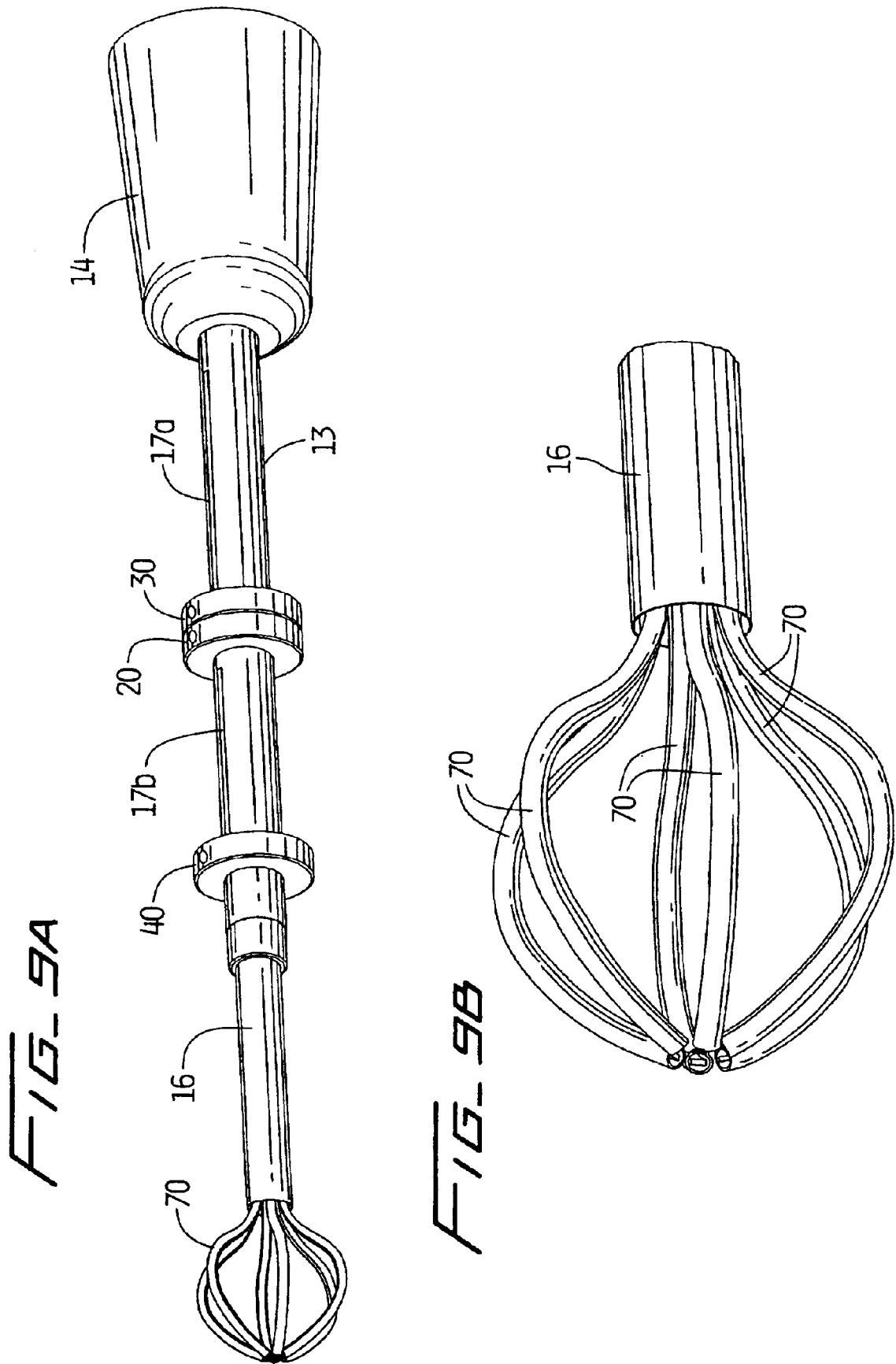

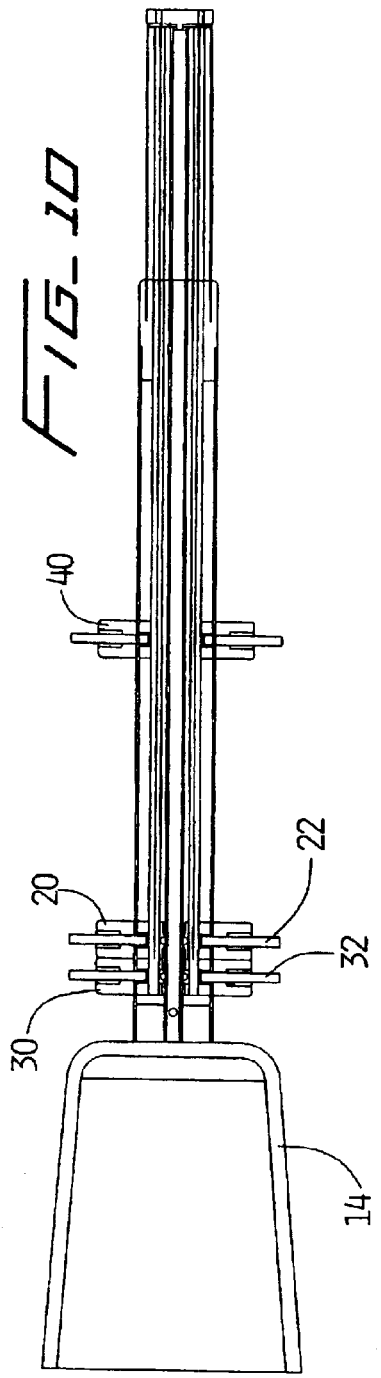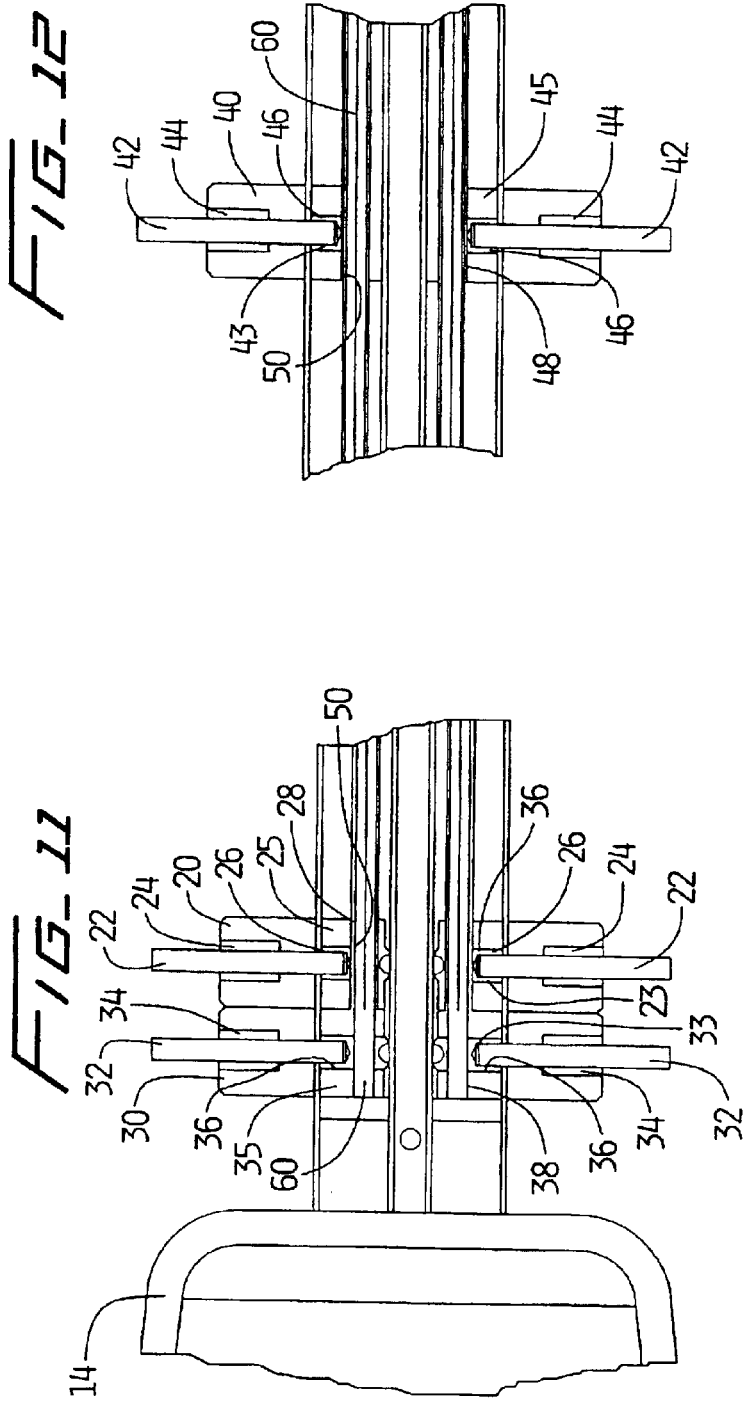

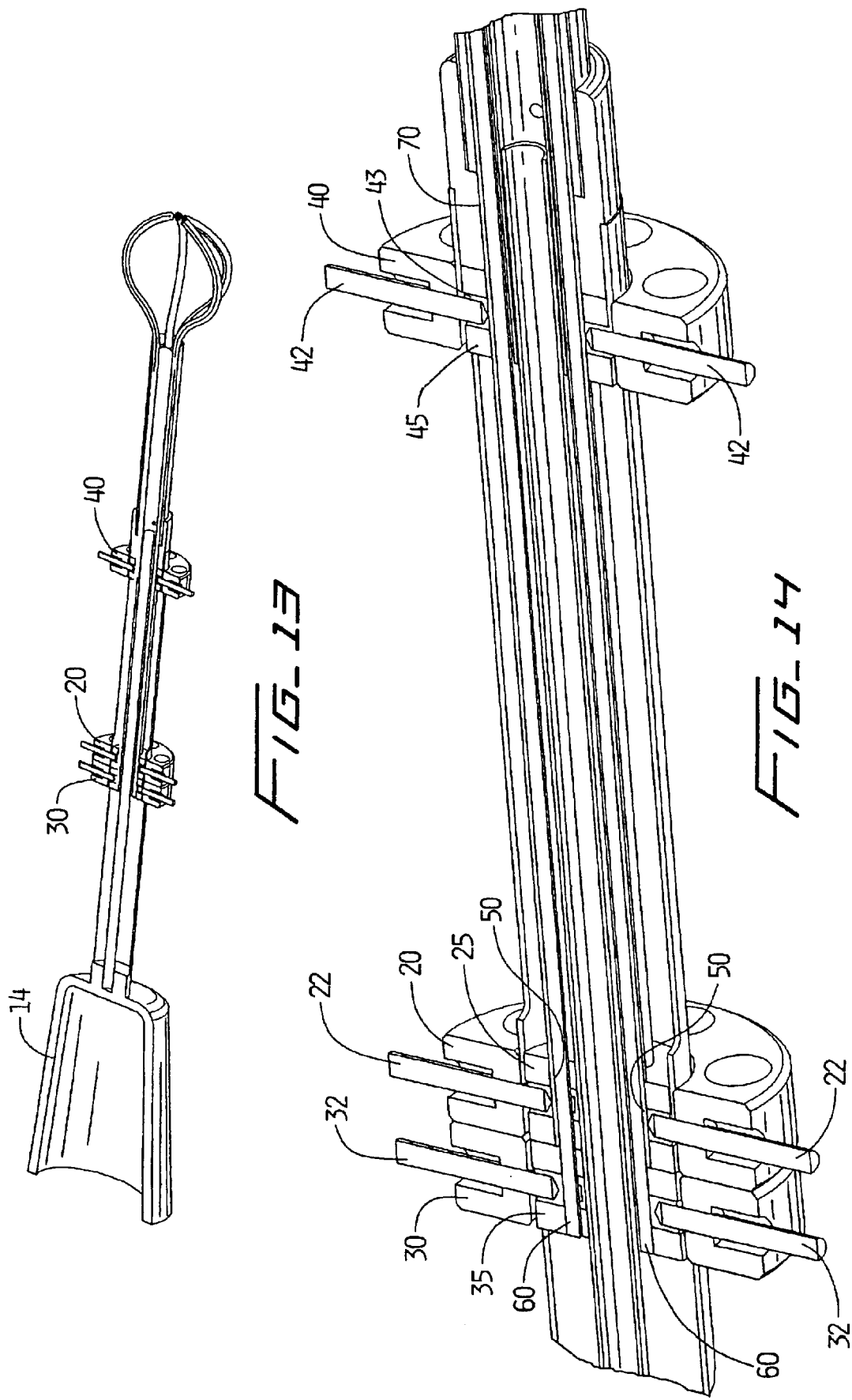

FIG_15
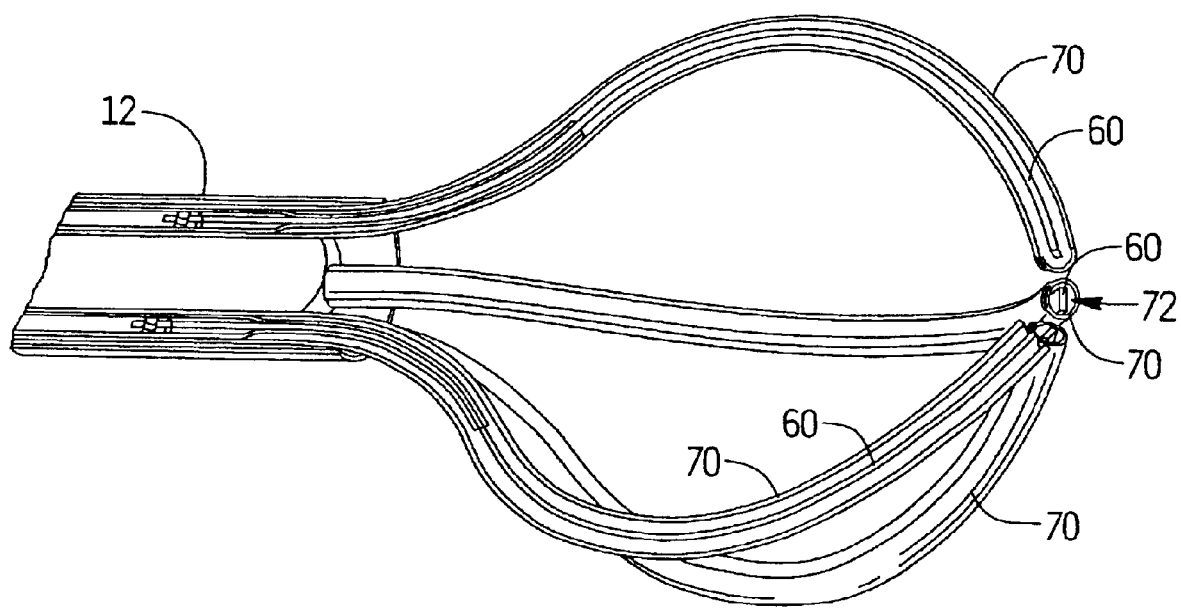
FIG_16
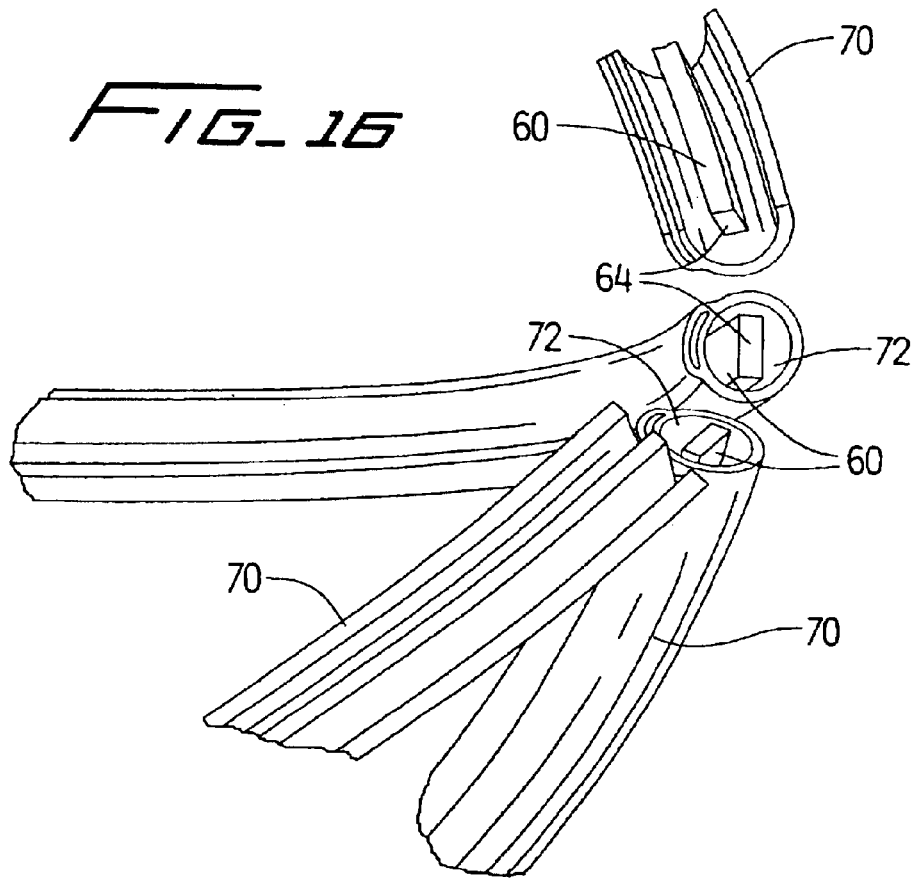

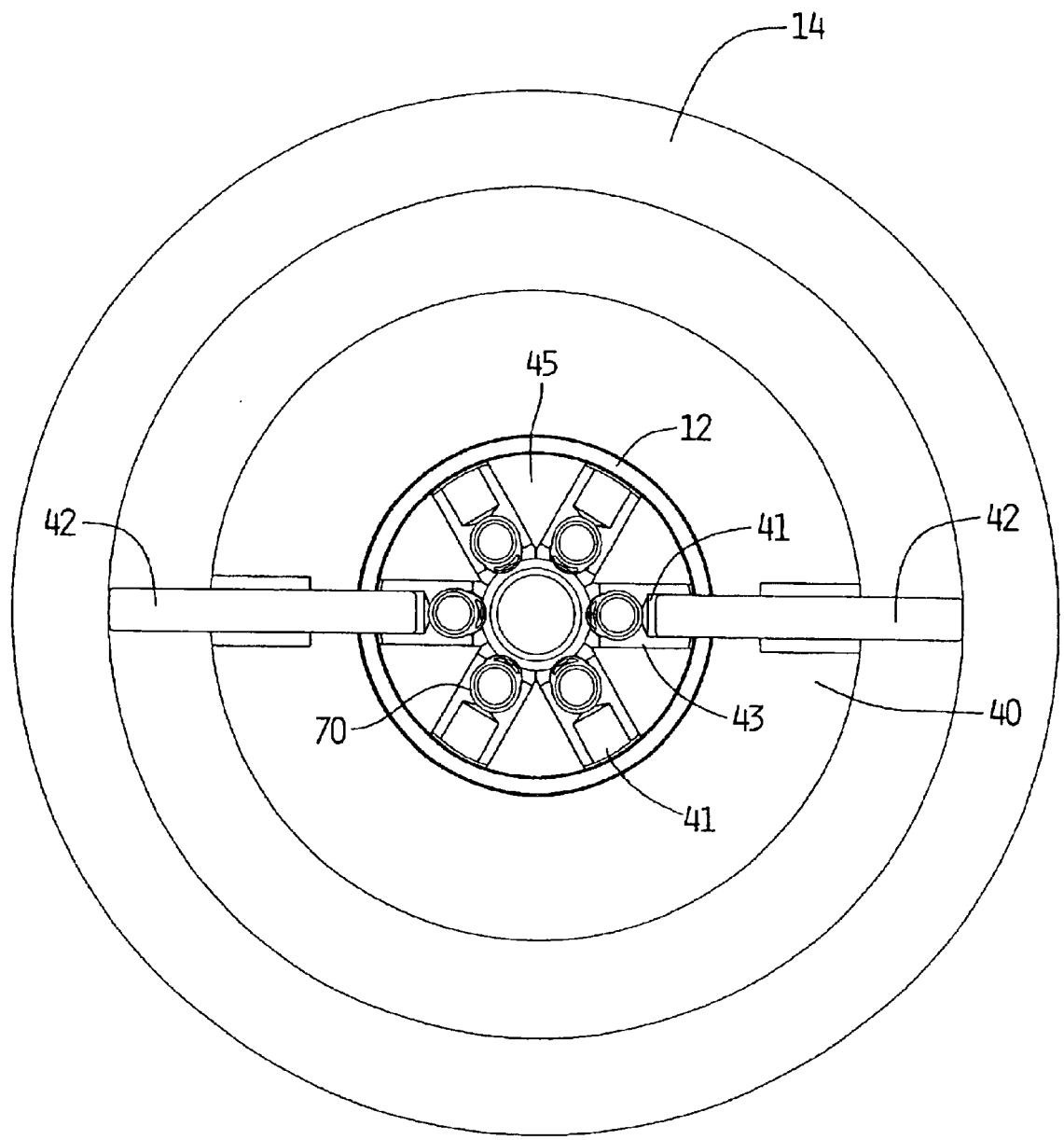
FIG_17A

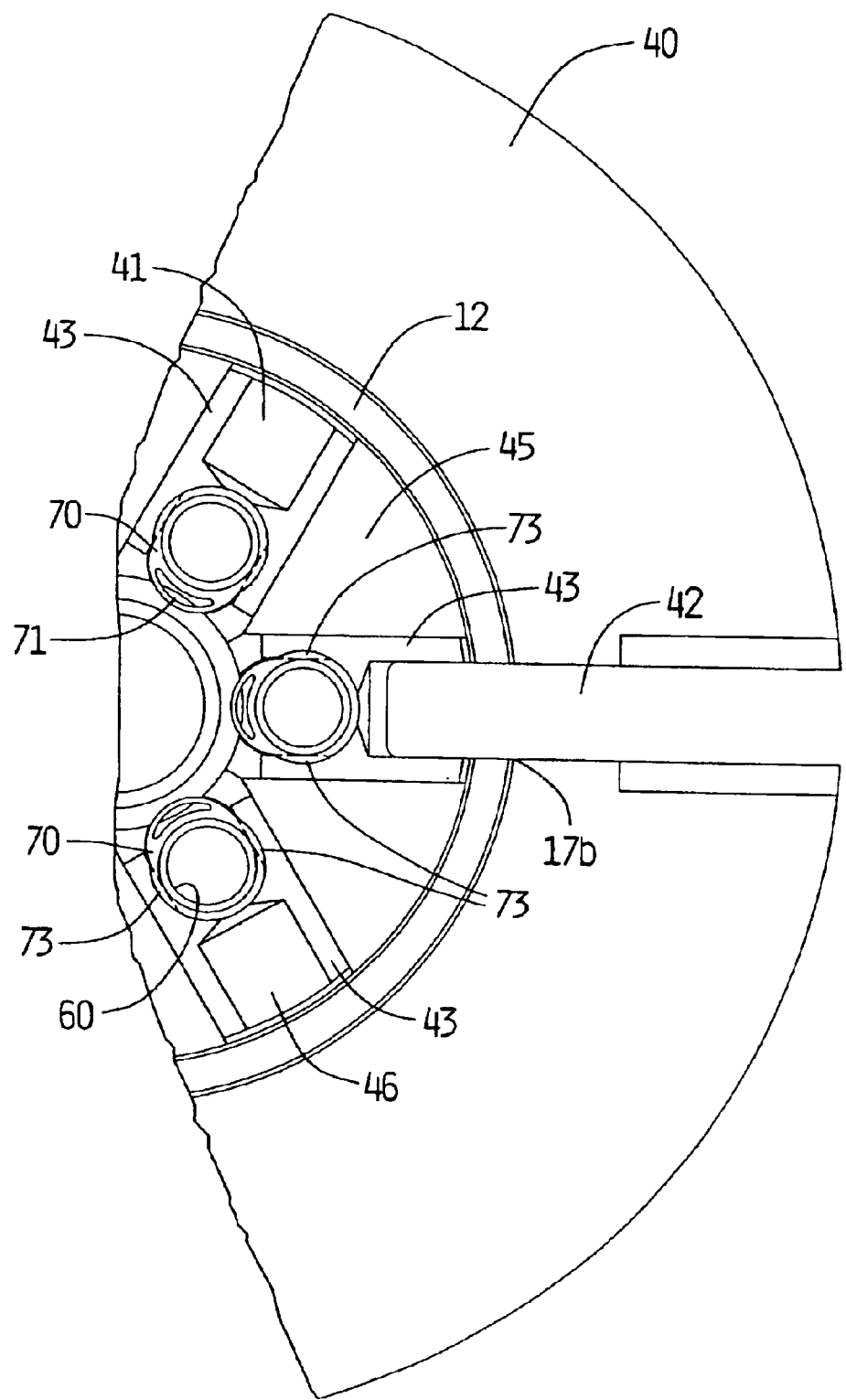
FIG_17B

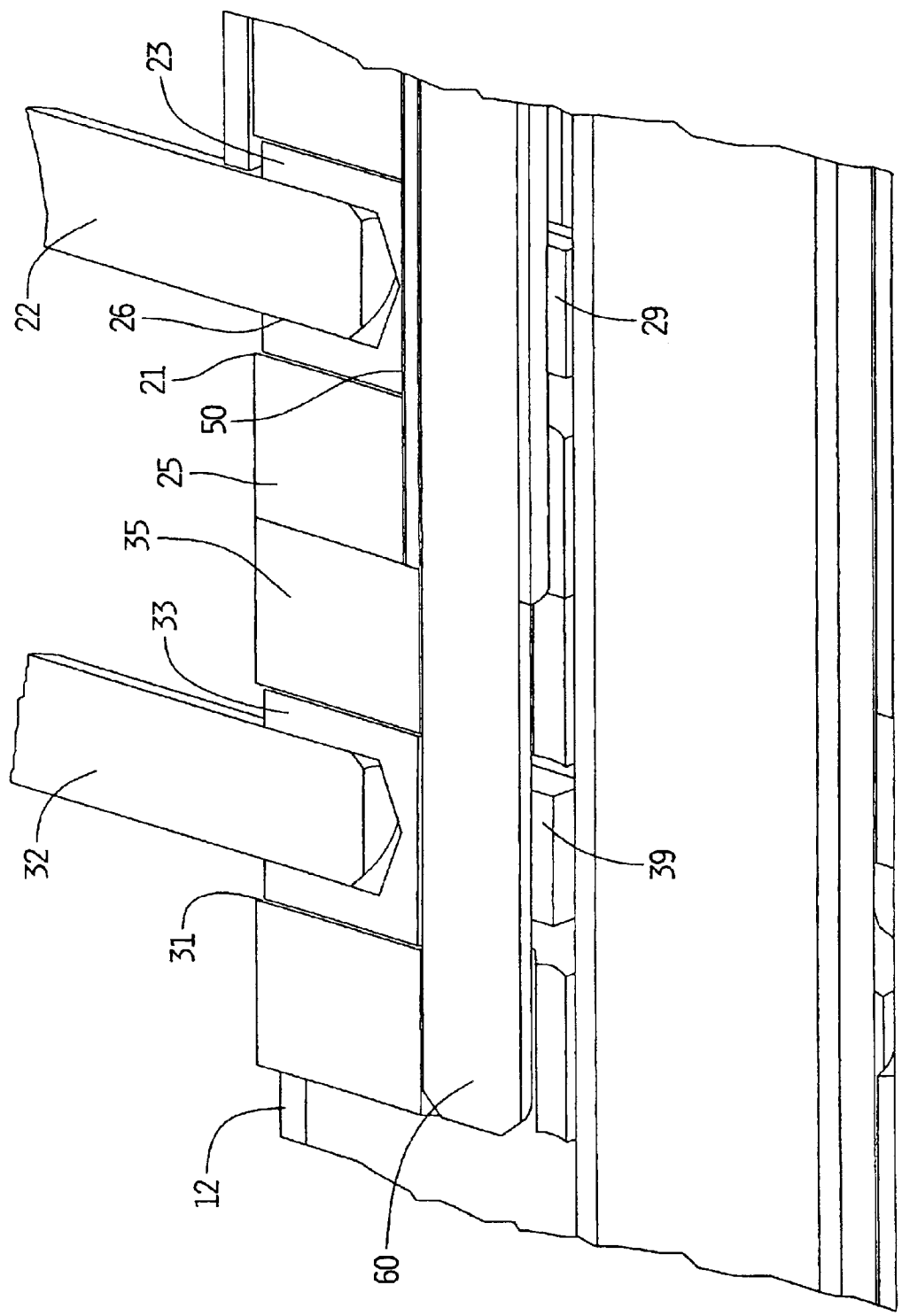

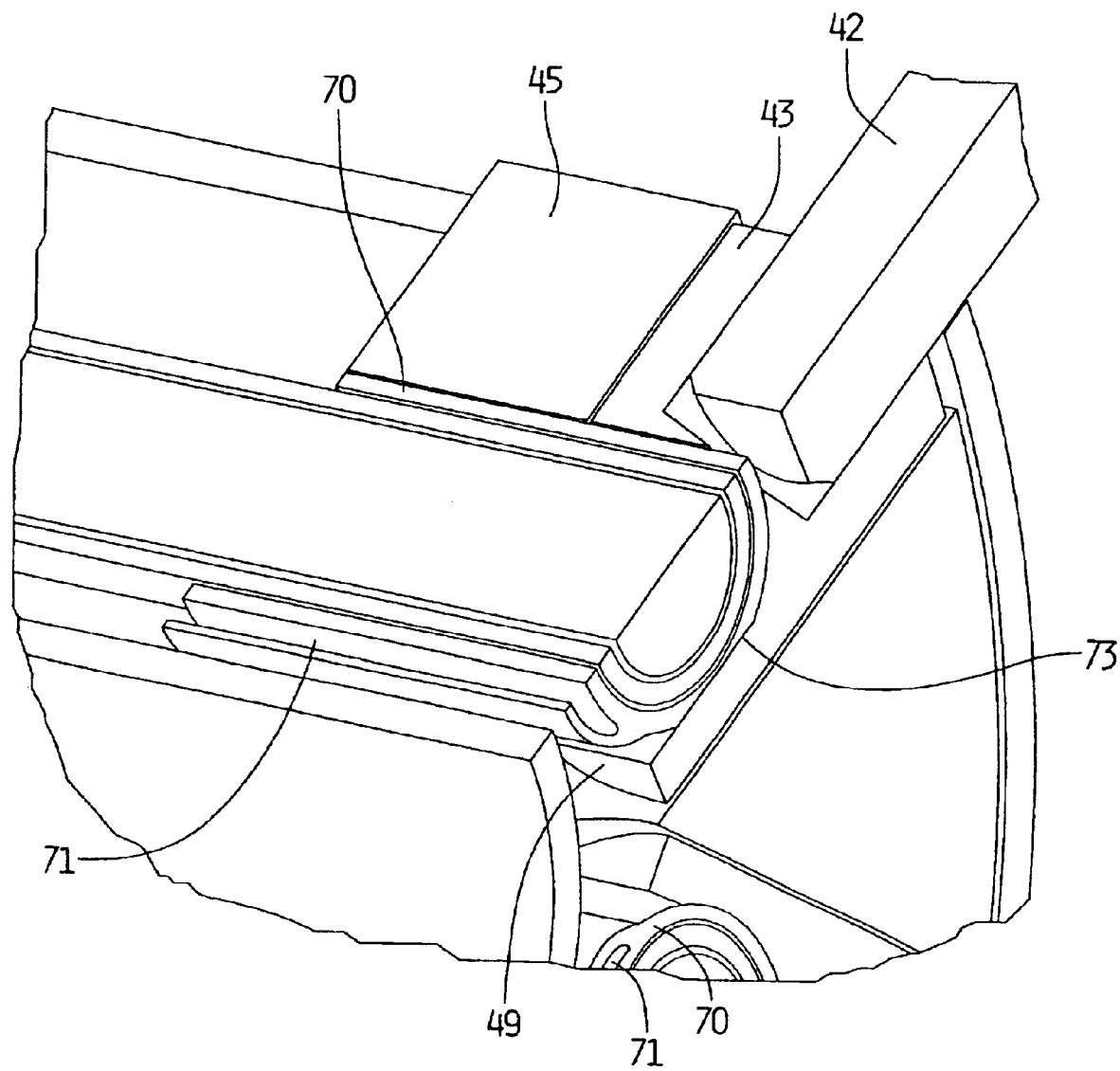

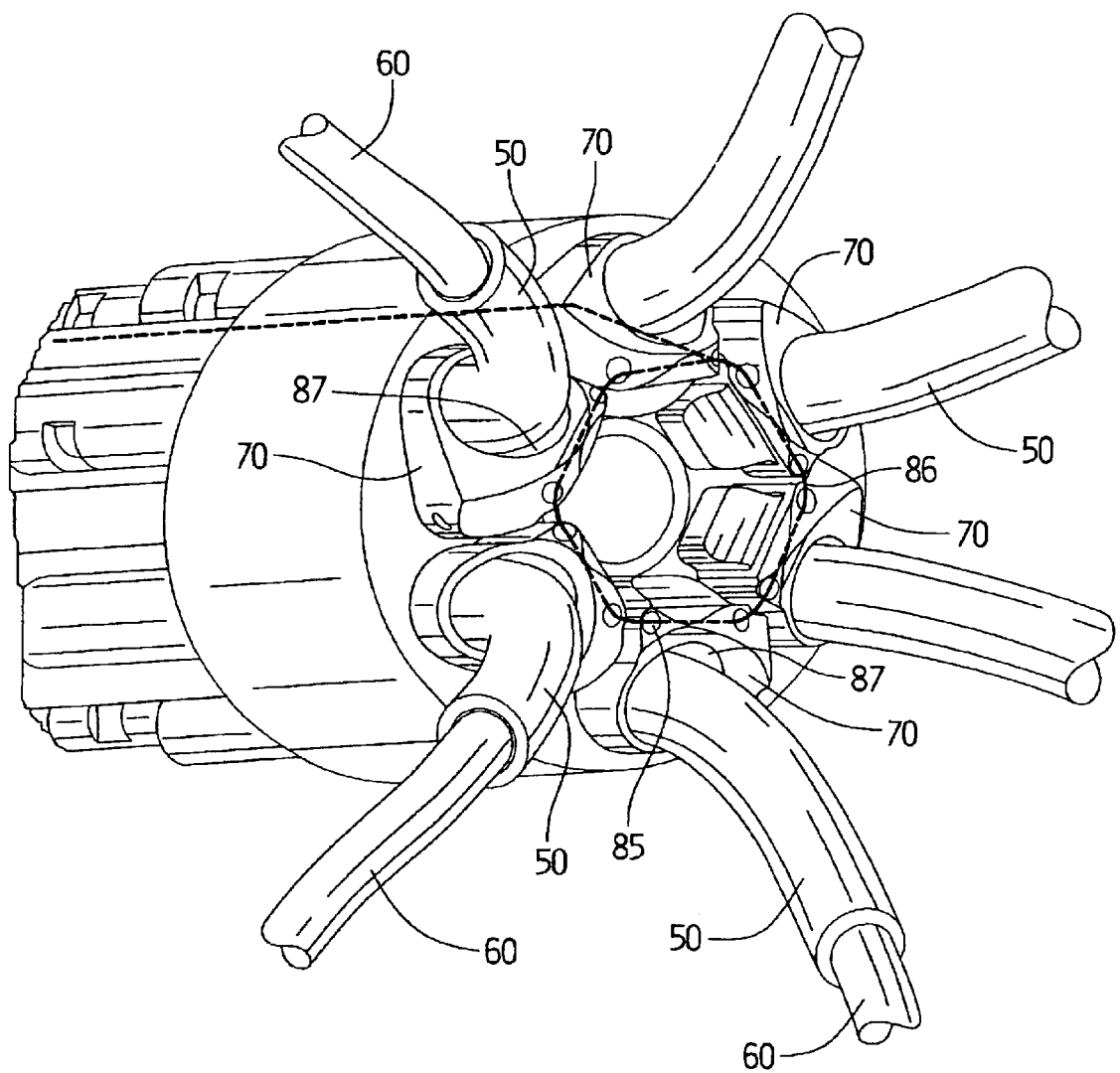
FIG_19

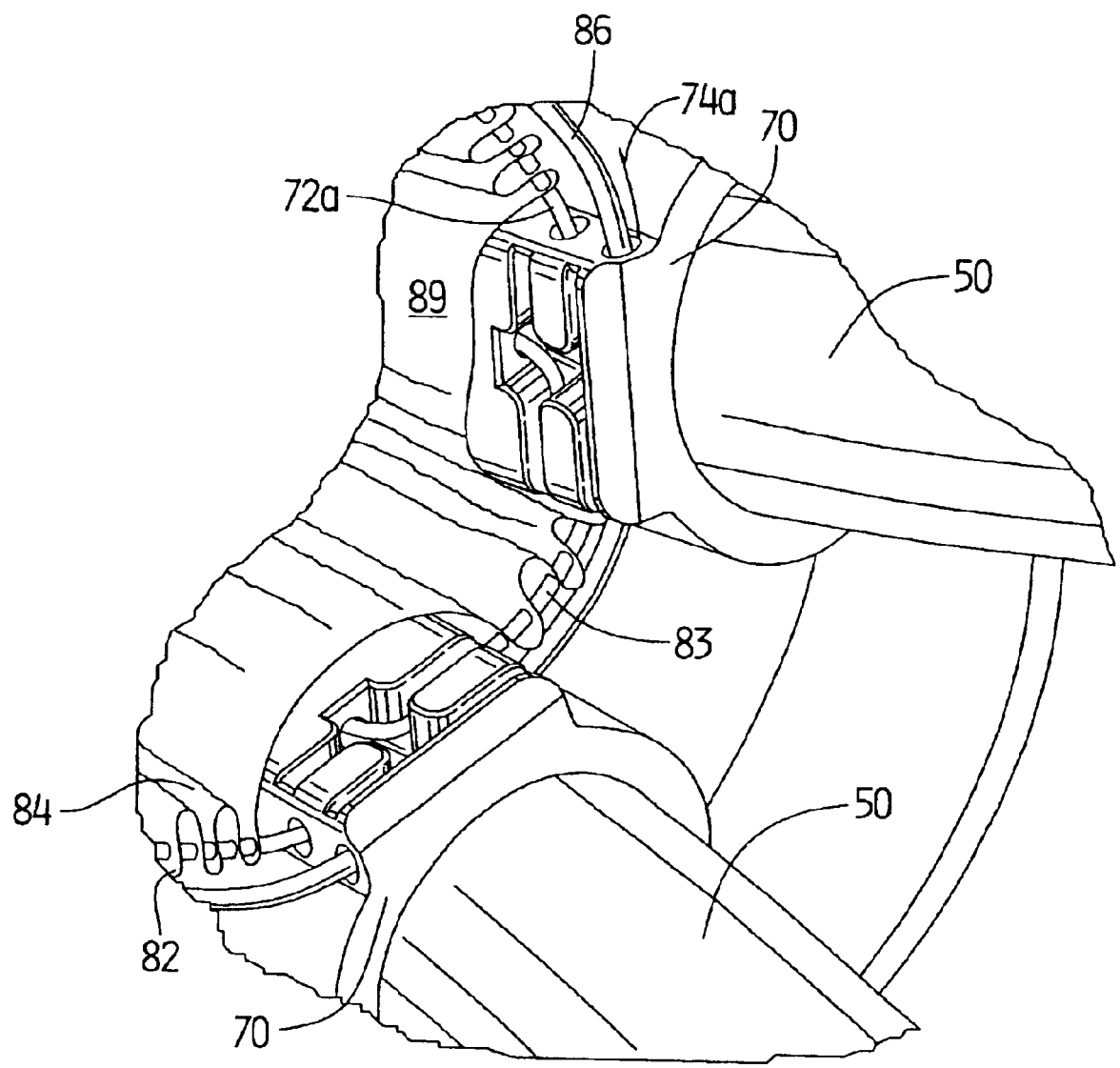
FIG_20

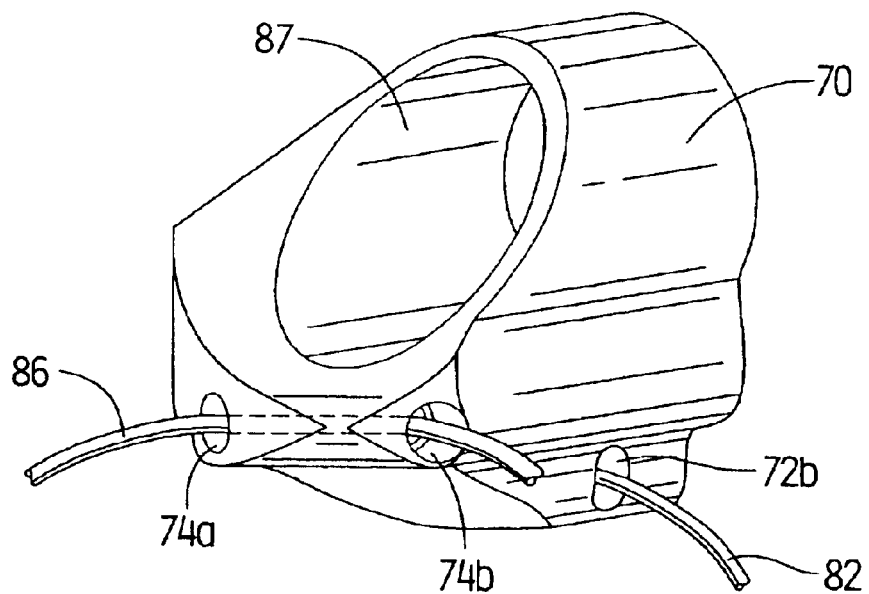
FIG_21A
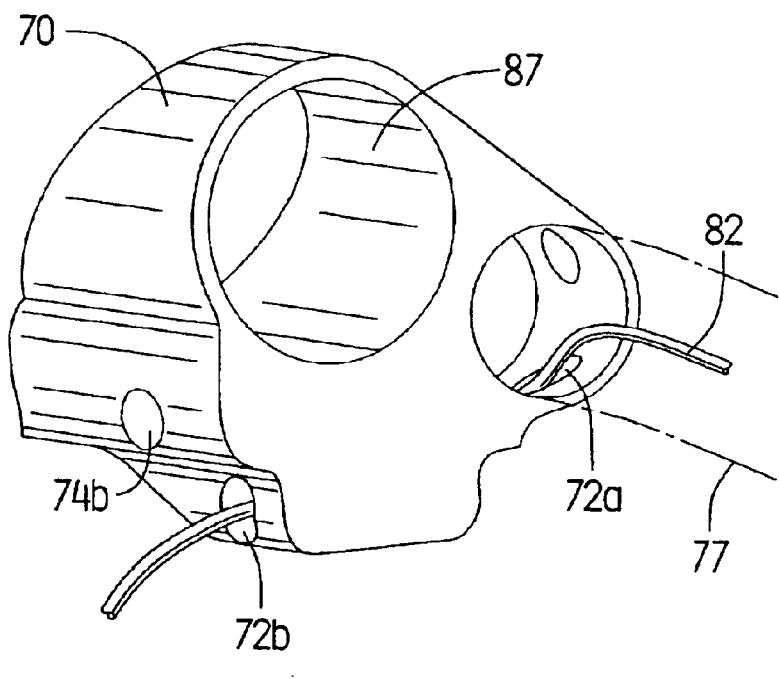
FIG_21B

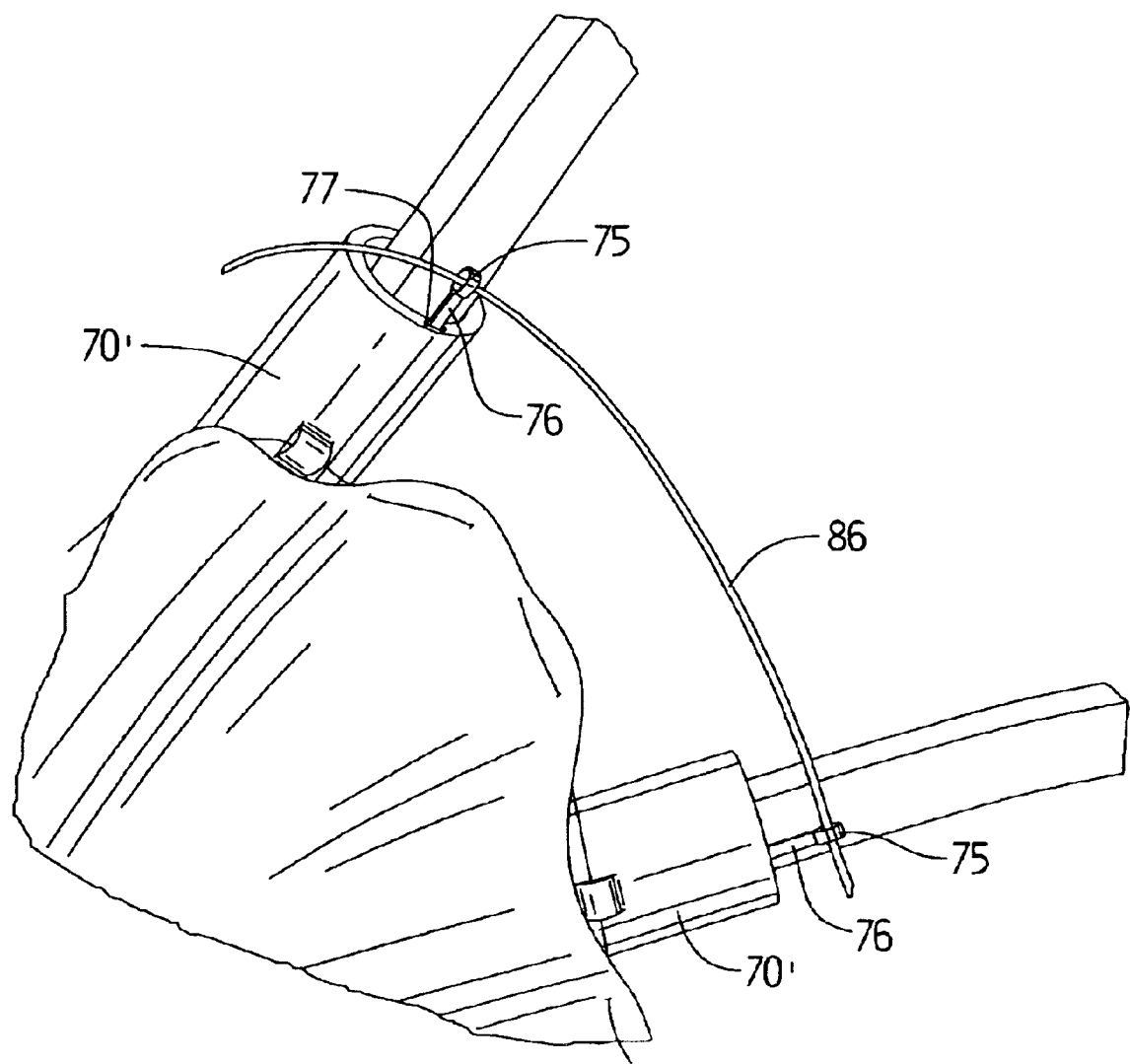
FIG_22

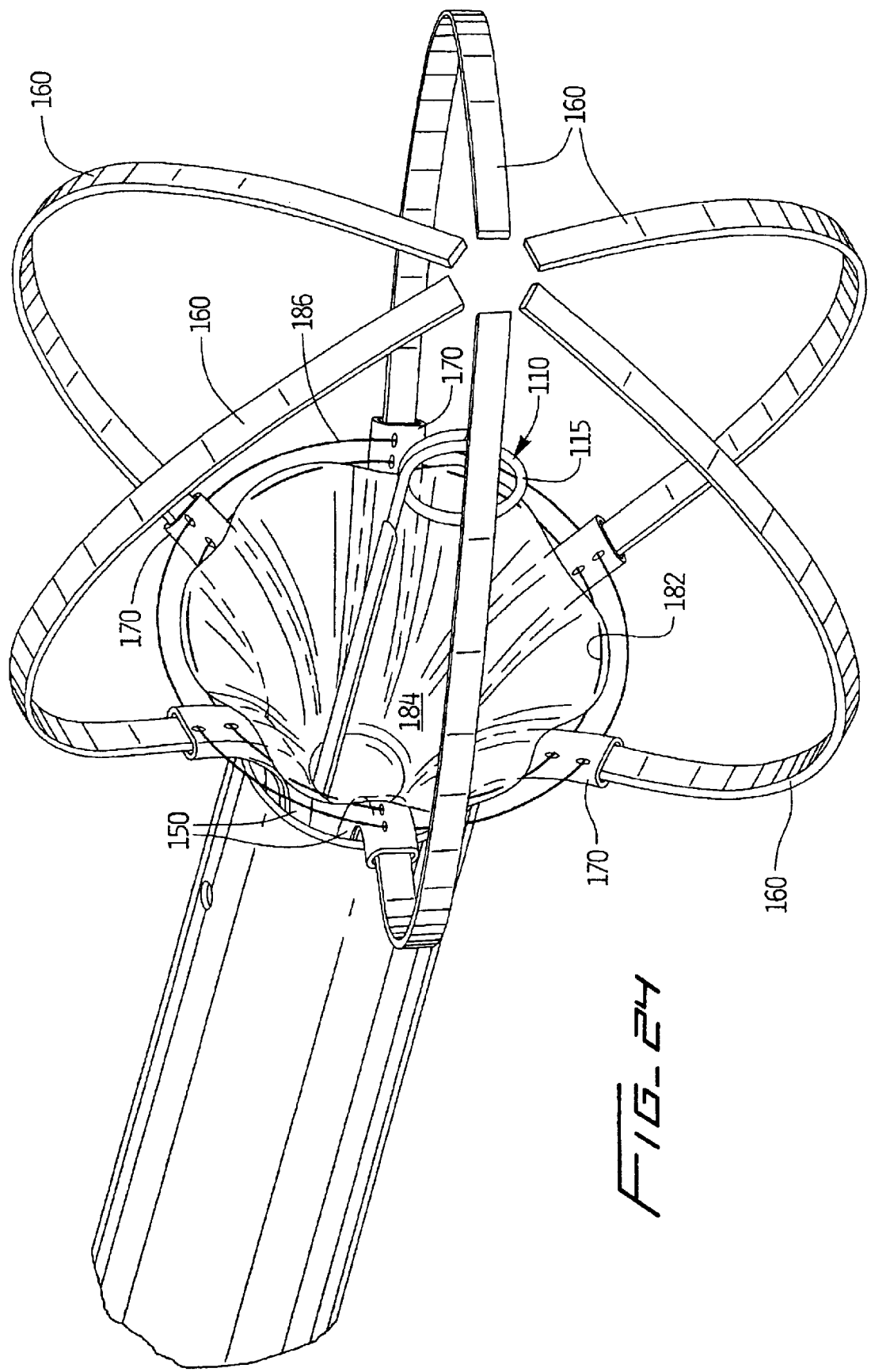

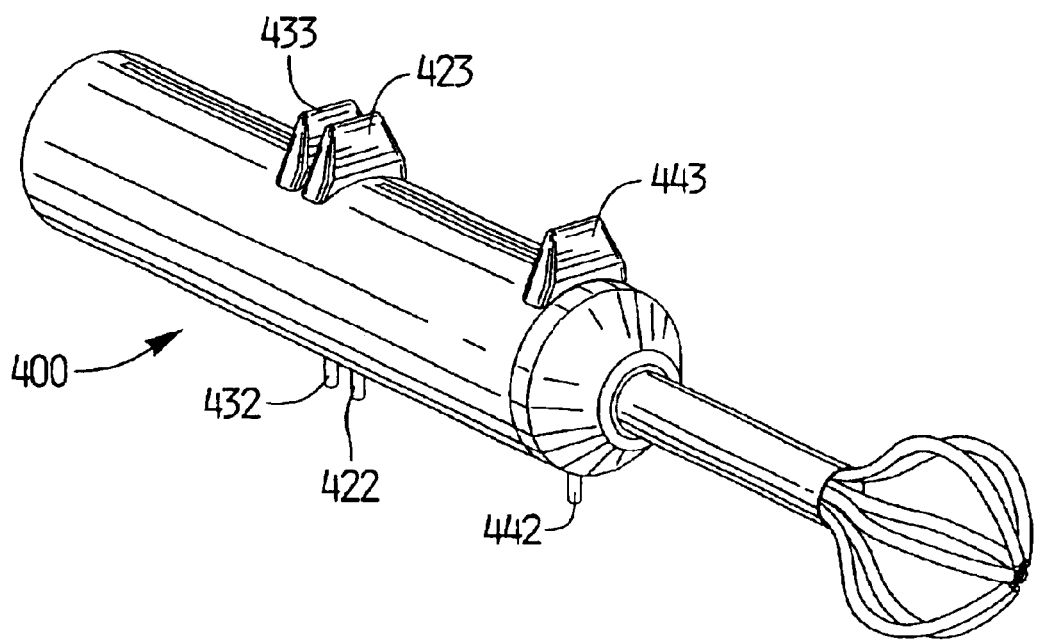
FIG_25
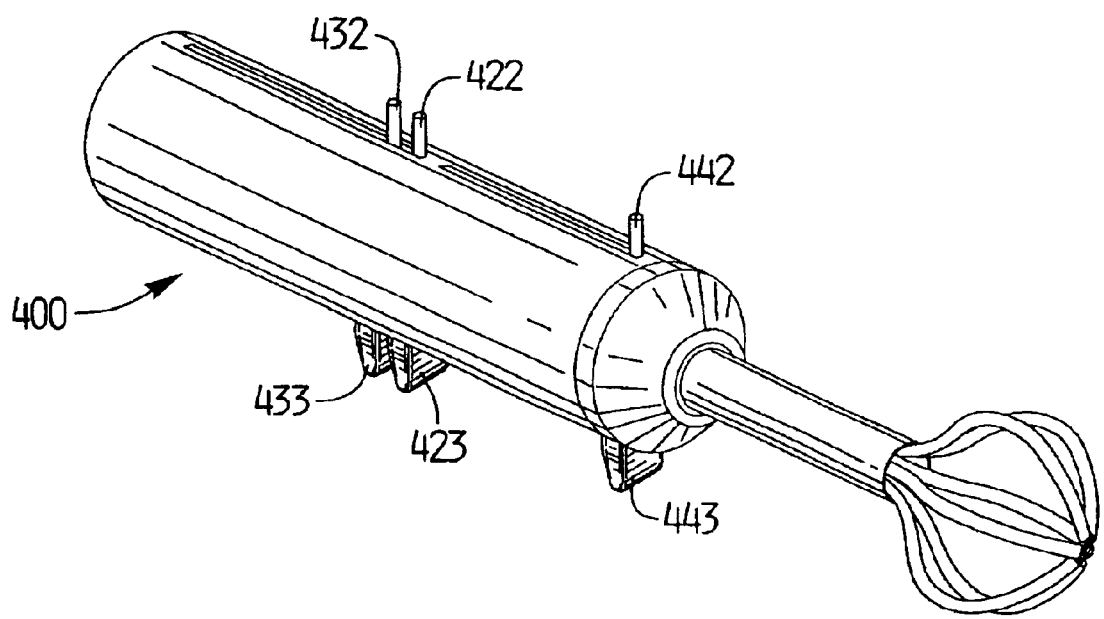
FIG_26

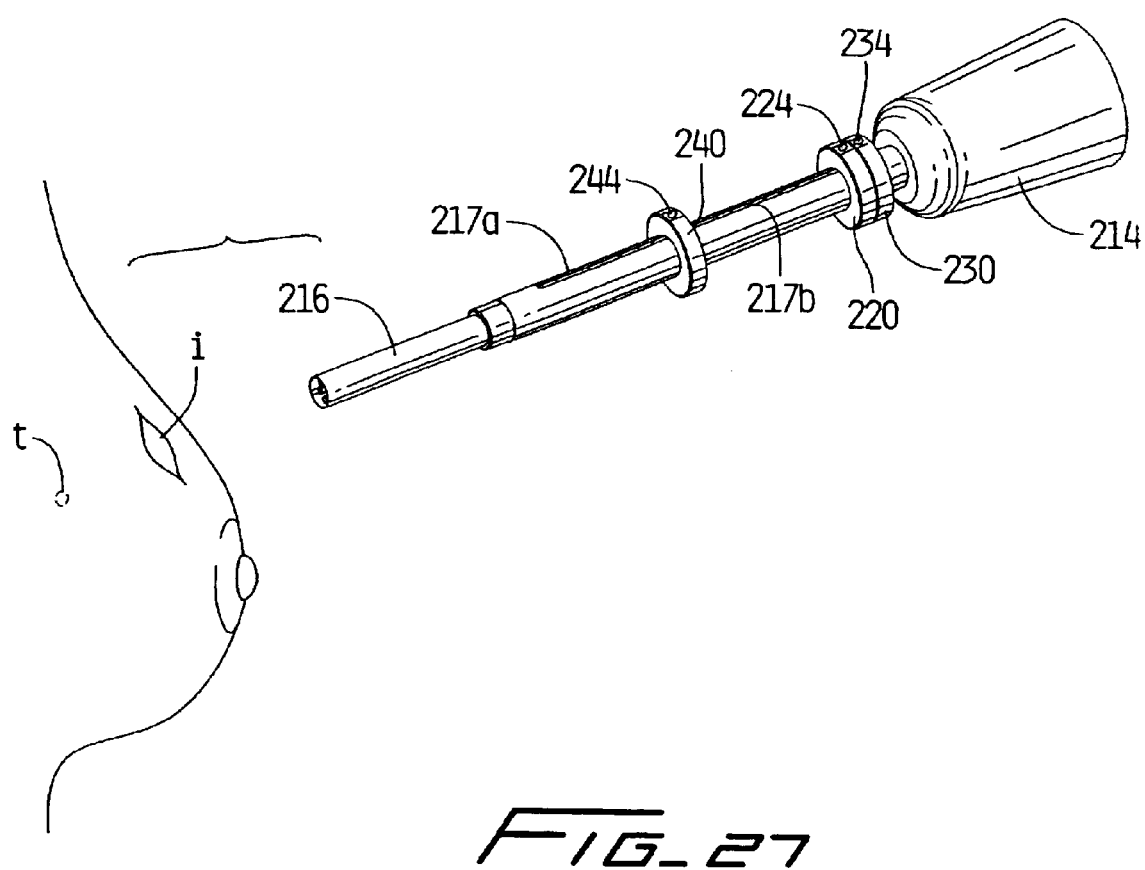
FIG_27

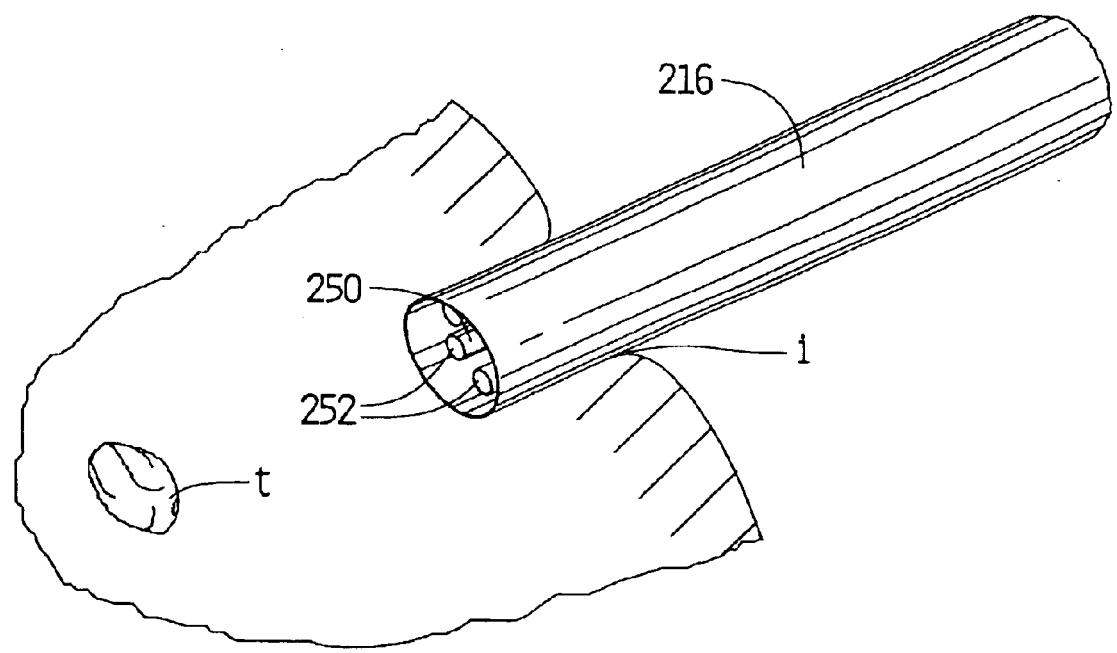
FIG_28
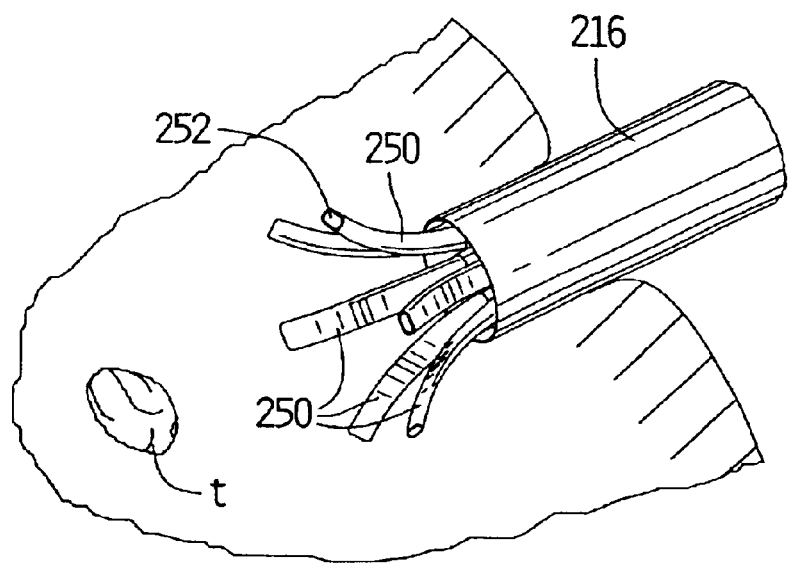
FIG_29

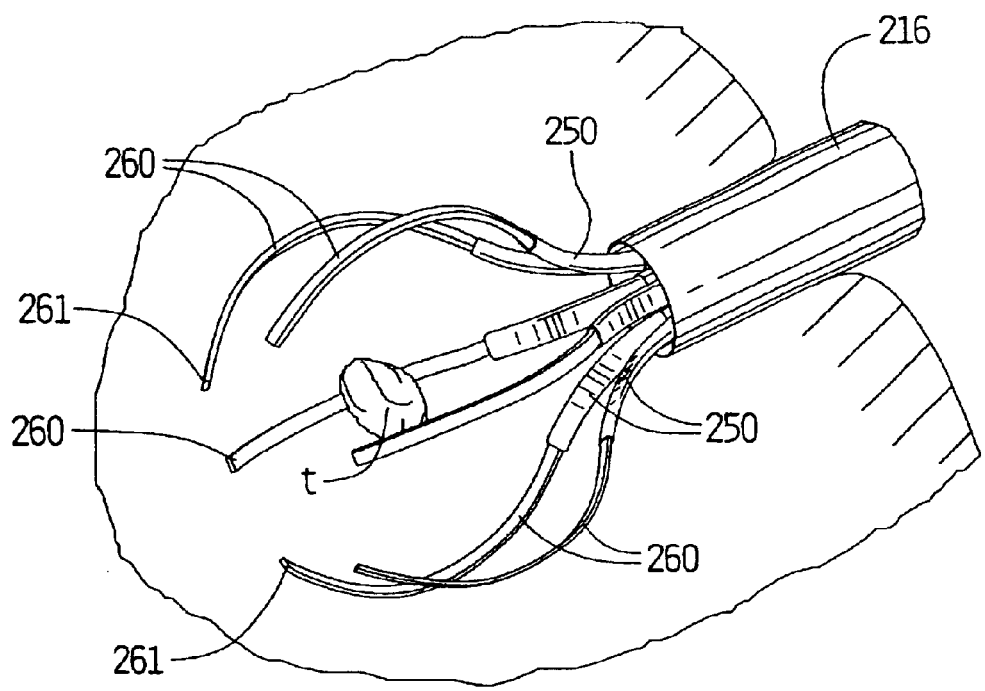
FIG_30
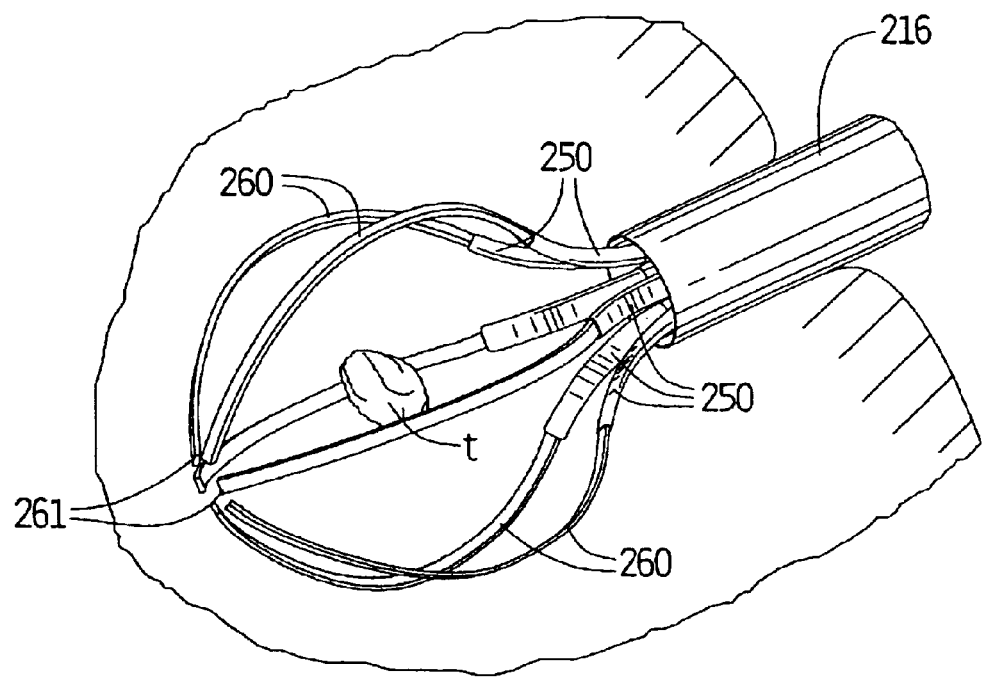
FIG_31

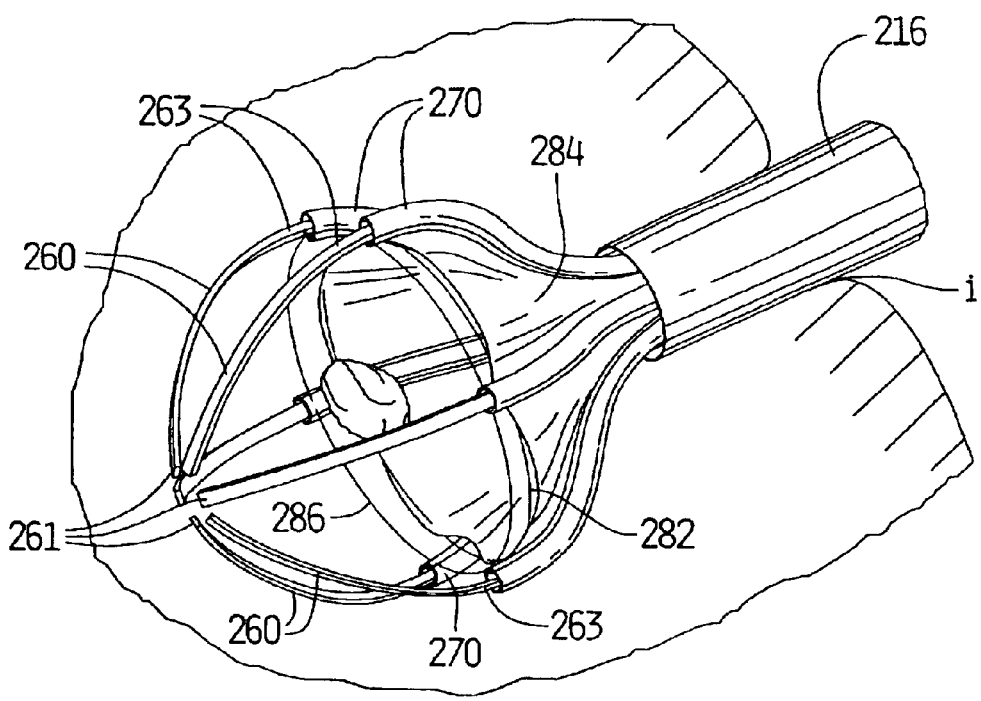
FIG_32
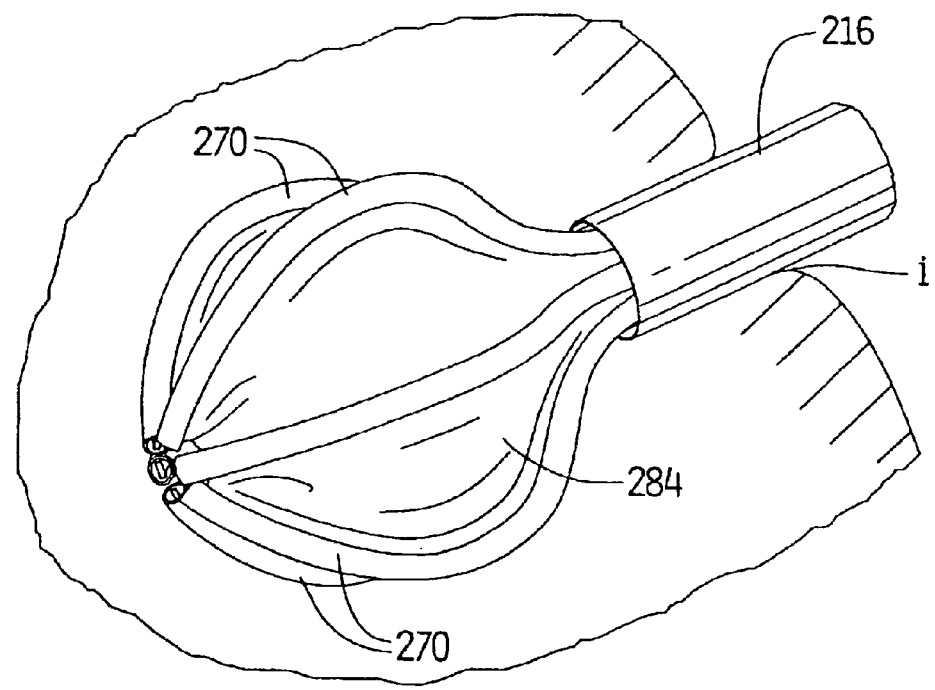
FIG_33

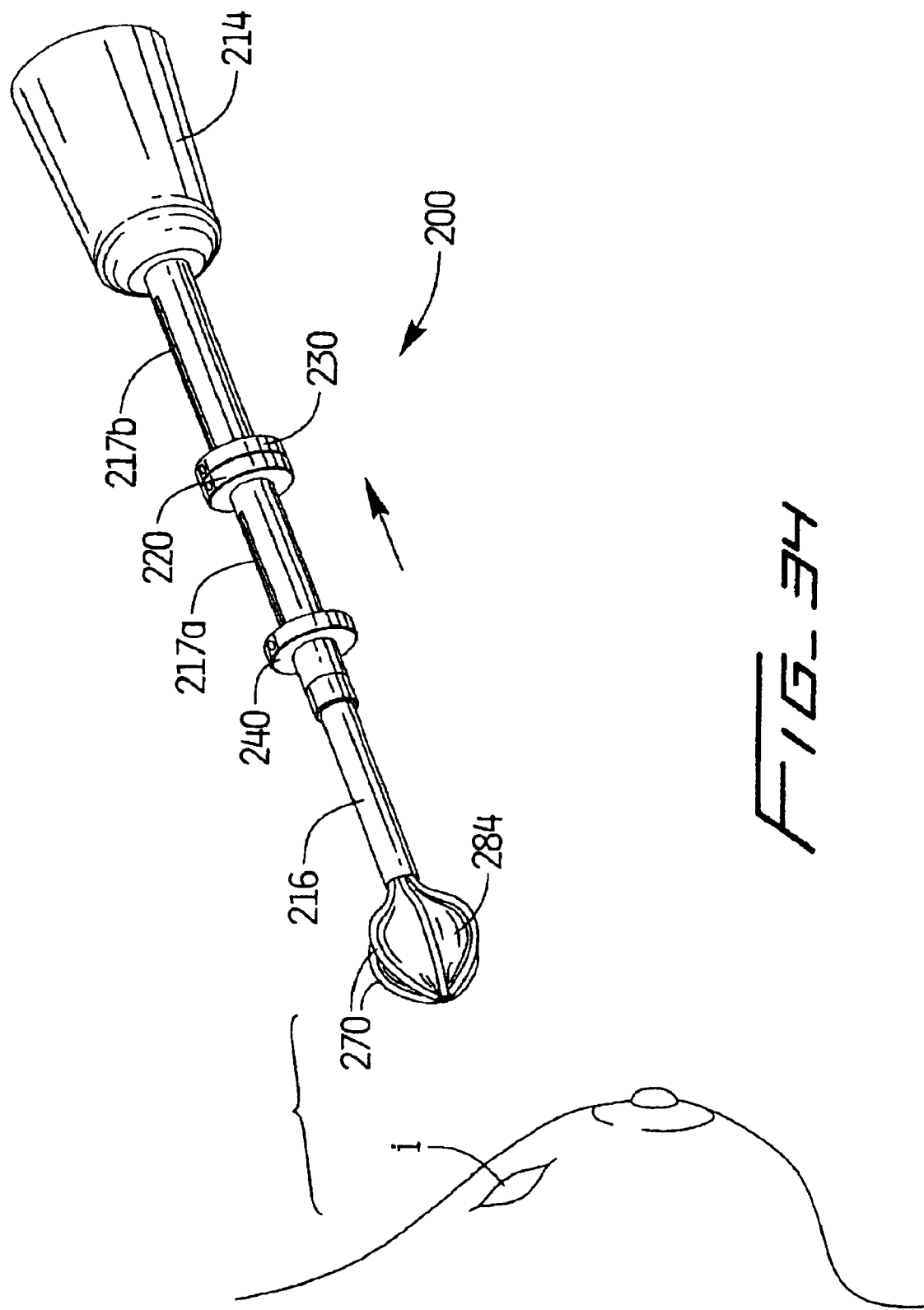

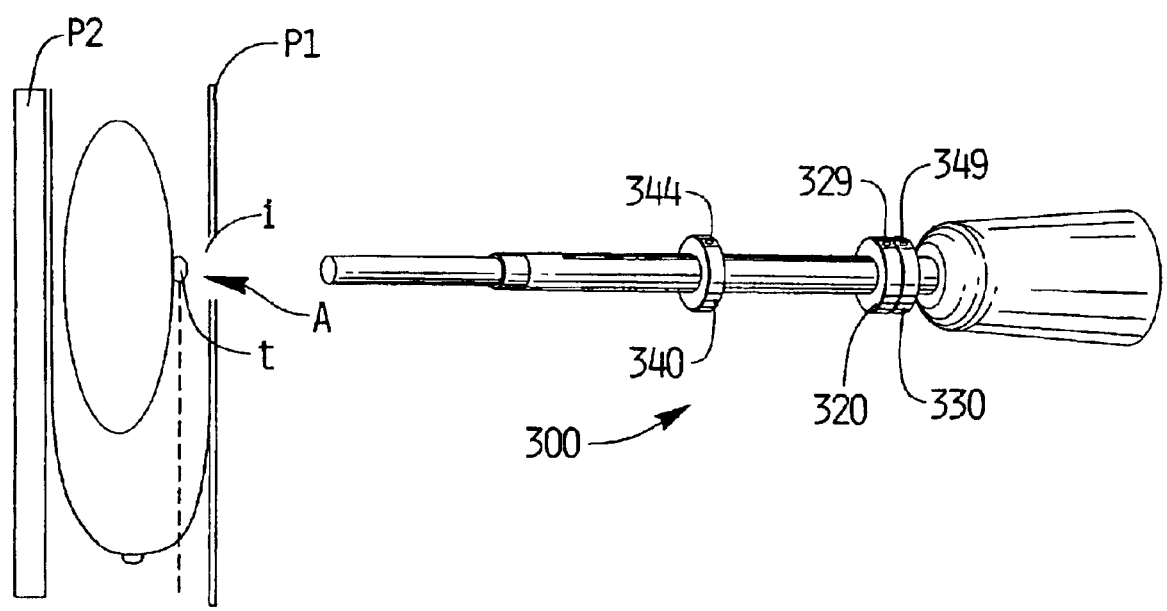
FIG_35

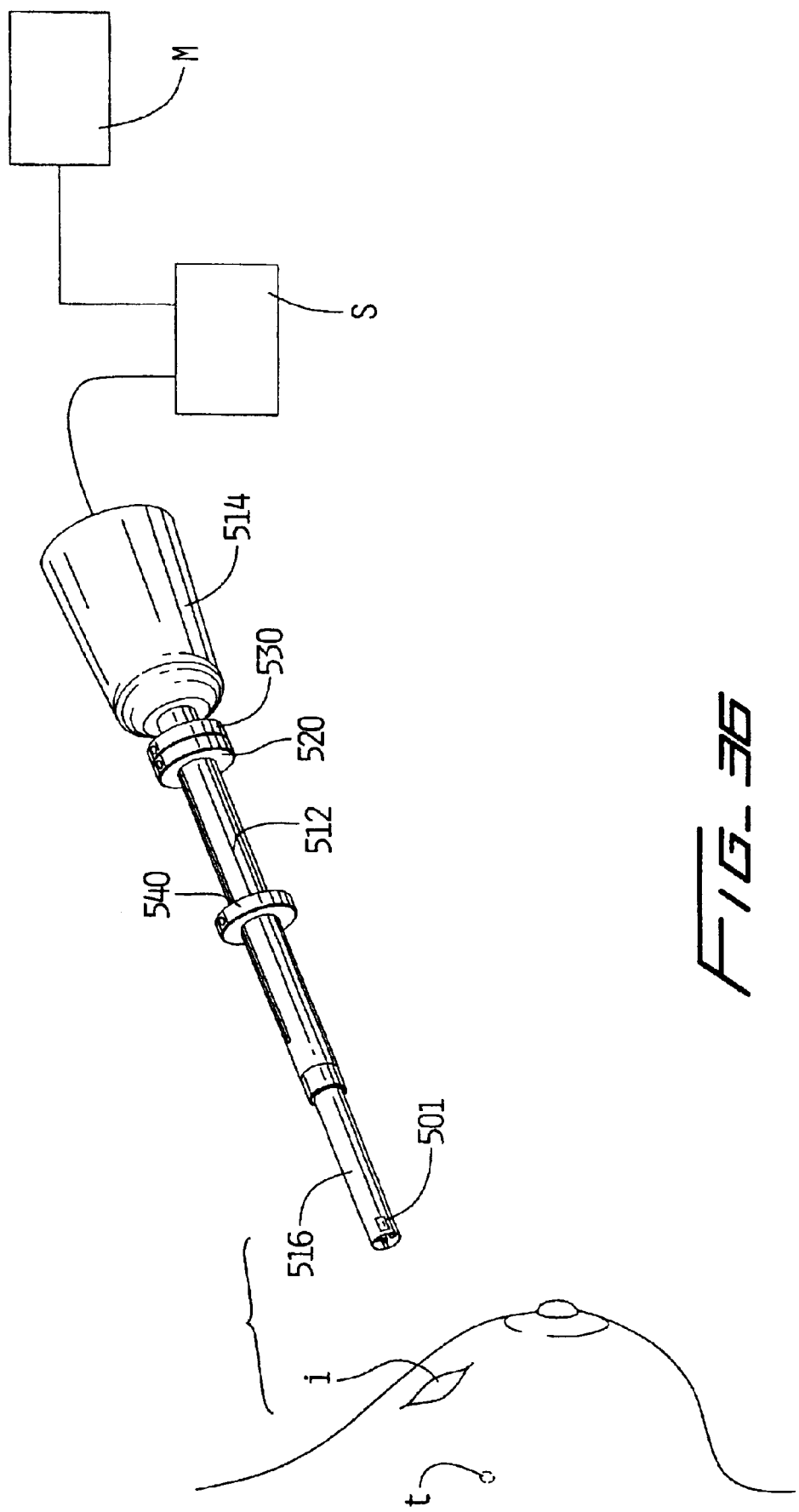

SURGICAL BIOPSY DEVICE

This application is a continuation of Ser. No. 09/844,729 filed Apr. 27, 2001 now U.S. Pat. No. 6,626,903 which is a continuation-in-part of U.S. patent application Ser. No. 09/122,185, filed Jul. 23, 1998 now U.S. Pat. No. 6,280,450 which claims priority from U.S. provisional application Ser. No. 60/053,664, filed Jul. 24, 1997. The contents of both these applications are incorporated herein by reference.

BACKGROUND

1. Technical Field

This application relates to a surgical device for removing tissue and more particularly relates to a surgical tissue biopsy device insertable through a small incision in the body.

2. Background of Related Art

Over 150,000 women in the United States alone are diagnosed each year with breast cancer. A biopsy of breast tissue is indicated when a breast abnormality is found, allowing removal of the tissue and testing to determine whether the abnormality is malignant and further surgery is necessary. Early diagnosis and removal of cancerous tissue is critical for successful treatment as early detection greatly increases the chances of survival.

Numerous devices are currently available for performing breast biopsies. These devices function to dissect a portion of the breast tissue and remove it from the body for pathology to determine whether the tissue is malignant.

The most invasive procedure is referred to as open excisional biopsy. In this procedure, large tissue samples are surgically removed, requiring long recovery times, risking disfigurement of the breast, increased scarring and increased morbidity.

In an attempt to overcome the disadvantages of open surgery, more minimally invasive instruments have been developed. One minimally invasive approach utilizes a percutaneous instrument referred to as a fine needle biopsy instrument. In this instrument, a needle and syringe are inserted directly through the breast into the target tissue, e.g. the lump, to remove a cell sample for pathology. One disadvantage of this technique is that numerous cell samples are required to be taken from the tissue to obtain a sufficient mass for testing, thereby requiring numerous needle sticks and increasing the time required for the procedure. Another disadvantage is that careful locational tracking of the tissue cells removed is required for accurate analysis. Also, with these devices there is a greater potential for false negatives due to the small sized specimens being removed without removal of sufficient surrounding areas of healthy tissue for comparison.

Another type of minimally invasive device is referred to as core needle biopsy. This device has a spring actuated cutter and obtains a larger specimen than the fine needle biopsy instruments. The specimen is suctioned into a side window in the needle and then back through the proximal end of the needle. Although larger than fine needle biopsy instruments, these needles are still relatively small, e.g. 2 mm in diameter. Since typically removal of between five and twenty tissue cores of 2 mm in diameter and 20 mm in length is required for accurate pathology, five to twenty needle sticks into the patient of this 2 mm diameter needle is required. These devices also have the disadvantage that the spring force cutting action may displace malignant cells into the adjacent normal tissue. Also, the amount of false negatives can be high because of inadequate removal of surrounding healthy tissue. Like fine needle biopsy, success and accuracy of the procedure is skill dependent because the device must be maneuvered to various positions and these different positions accurately tracked.

Another disadvantage common to both fine needle and core needle biopsy devices is that the entire lesion cannot be removed. Therefore, if the tests show the lesion is malignant, another surgery must be scheduled and performed to remove the entire lesion and surrounding tissue. Besides the additional cost and surgeon time, this can have an adverse psychological affect on the patient who must await the second surgical procedure.

Some percutaneous devices, such as the Mammotome marketed by Ethicon, Inc., attempted to overcome some of these disadvantages of percutaneous devices by enabling multiple specimens to be removed with a single needle stick. The specimens are removed from the proximal end of the needle by a vacuum. Although overcoming some disadvantages such as reducing the number of needle sticks, the Mammotome still fails to overcome many of the other drawbacks since careful tracking is required, success is skill dependent, and a second surgery is necessary if the lesion is malignant, with the attendant expenses and trauma.

In an attempt to avoid a second procedure, the ABBI instrument marketed by United States Surgical Corporation provided a larger needle so that the entire specimen and tissue margins could be removed. The extra tissue excised is achieved by a larger diameter cannula. The cannula removes breast tissue from the skin surface entry point to the interior region of the breast where the lesion is located. The advantage of this instrument is that if pathology indicates the tumor is malignant, then an additional surgical procedure is not necessary since the tumor and margins were removed by the large cannula. However, a major disadvantage of this instrument is that if pathology indicates the lesion is benign, then a large tissue mass would have been unnecessarily removed, resulting in more pain, a larger scar, and possible disfigurement of the breast. Thus, ironically, the instrument is more beneficial if the tumor is malignant, and disadvantageous if the tumor is benign. In either case, the instrument has the further disadvantages of causing additional bleeding because of the large incision and requiring closure of a larger incision, thereby increasing scarring, lengthening patient recovery time, and adding to the cost, time and complexity of the procedure.

It would therefore be advantageous to provide a surgical breast biopsy device which can access the targeted lesion through a small incision but be able to remove the entire lesion and margin, thereby avoiding the necessity for a second surgery. Such device would advantageously reduce the risk of cancer seeding, provide more consistent testing, reduce surgery time, reduce bleeding, and minimize disfigurement of the patient's breast.

SUMMARY

The present invention overcomes the foregoing deficiencies and disadvantages of the prior art. The present invention provides a surgical biopsy apparatus for cutting tissue comprising a housing having a longitudinal axis, first and second members movable from a retracted position to an extended position with respect to the housing, a third member slidably positioned and extendable with respect to the first member, a fourth member slidably positioned and extendable with respect to the second member, and an electrocautery cutting wire movable with respect to the third and fourth members to surround a region of tissue positioned between the third and fourth members to cut the tissue.

The apparatus preferably further includes a tissue retrieval bag movable with respect to the third and fourth members and movable from a retracted position within the housing to an extended position distally of the housing to surround a region of tissue positioned between the third and fourth members to remove the cut tissue.

The apparatus preferably further comprises a first carrier slidably positioned over the first and third member, wherein the first carrier supports and advances the electrocautery wire and a suture for closing the tissue retrieval bag Preferably the first and second members move radially outwardly away from the longitudinal axis of the housing and the third and fourth members initially move radially outwardly away from the longitudinal axis followed by movement inwardly towards the longitudinal axis. The third member is preferably telescopingly received within a first channel in the first member and the fourth member is preferably telescopingly received within a second channel in the second member.

The present invention also provides a surgical biopsy apparatus for cutting a tissue mass comprising a housing, a plurality of first members extendable with respect to the housing and movable in a first direction at a first angle to the longitudinal axis of the housing, a plurality of second members movable with respect to the first members in a second direction different than the first direction and at an angle to the first angle, and a cutting wire movable longitudinally with respect to the first and second members to cut the tissue mass.

The apparatus preferably includes a tissue retrieval bag movable longitudinally with respect to the first and second members to remove the tissue mass cut by the cutting wire. Preferably, a loop of the cutting wire and a mouth of the tissue retrieval bag are enlarged by the plurality of first and second members.

The apparatus may include a marker supported within the housing and insertable into the tissue mass, the marker composed of shape memory material and the first and second members surrounding the marker. The first and second members may also be composed of shape memory material.

The present invention also provides a surgical biopsy apparatus comprising a housing, a plurality of members advanceable with respect to the housing to provide a boundary for an area of tissue to be removed, a cutting wire loop advanceable with respect to the plurality of members to cut the area of tissue and/or a tissue retrieval bag advanceable with respect to the plurality of members to remove the area of tissue. Preferably, the cutting wire loop and/or a mouth of the tissue retrieval bag is moved to a larger diameter as it is advanced with respect to the members. Preferably at least one carrier is provided which is advanceable over one of the plurality of members to advance the cutting wire and the tissue retrieval bag toward the target tissue.

The apparatus may also include an ultrasonic transducer at a distal end of the housing to enhance ultrasound imaging during the biopsy procedure.

The present application also provides a method for removing a tissue mass for biopsy comprising inserting a cannula to a position proximal of the target tissue mass, advancing a plurality of tissue penetrating members from the cannula to an angular position to create a boundary area around the tissue mass, and advancing an electrocautery cutting wire with respect to the tissue penetrating members to surround the tissue mass defined within the boundary area.

The method may further comprise the step of advancing a tissue containment bag with respect to the tissue penetrating members to encapsulate the cut tissue mass for removal, wherein the cutting wire and tissue containment bag are advanced substantially simultaneously.

A method for performing breast biopsy is also provided comprising inserting into breast tissue a housing having a diameter smaller than a diameter of the tissue to be biopsied, advancing penetrating members through the breast tissue to create a tissue boundary area having a transverse cross-sectional length greater than the diameter of the housing, and advancing a cutting wire so a loop of the cutting wire moves to a diameter greater than the diameter of the housing.

BRIEF DESCRIPTION OF THE DRAWINGS

Preferred embodiment(s) of the present disclosure are described herein with reference to the drawings wherein:

FIG. 1A is a perspective view of the biopsy apparatus of the present invention in the initial position;

FIG. 1B is an enlarged perspective view of the distal end portion of the apparatus of FIG. 1A showing the outer (female) rails in the retracted position;

FIG. 2A is a perspective view of the apparatus of FIG. 1 showing the outer and inner (male) rails in the fully deployed (advanced) position;

FIG. 2B is an enlarged perspective view of the distal end portion of the apparatus of FIG. 2A;

FIG. 3A is a perspective view of the apparatus of FIG. 1 showing the outer rails in the fully deployed position;

FIG. 3B is an enlarged perspective view of the distal end portion of the apparatus of FIG. 3A;

FIG. 4A is a perspective view of the apparatus of FIG. 1 showing the outer rails in the fully deployed position and the inner rails slightly advanced from within the outer rails;

FIG. 4B is an enlarged perspective view of the distal end portion of the apparatus of FIG. 4A;

FIG. 5A is a perspective view of the apparatus of FIG. 1 showing the outer rails in the fully deployed position and the inner rails partially advanced from within the outer rails;

FIG. 5B is an enlarged perspective view of the distal end portion of the apparatus of FIG. 5A;

FIG. 6A is a perspective view of the apparatus of FIG. 1 showing the outer rails in the fully deployed position and the inner rails further advanced to an intermediate position;

FIG. 6B is an enlarged perspective view of the distal end portion of the apparatus of FIG. 6A;

FIG. 7A is a perspective view of the apparatus of FIG. 1 showing the outer rails in the fully deployed position, the inner rails in the fully deployed (advanced) position, and the carriers initially advanced over the outer rails; (the cutting wire, suture, and bag being removed for clarity);

FIG. 7B is an enlarged perspective view of the distal end portion of the apparatus of FIG. 7A;

FIG. 8A is a perspective view of the apparatus of FIG. 1 showing the outer rails in the fully deployed position, the inner rails in the fully deployed position, and the carriers partially advanced over the inner rails past an intermediate position;

FIG. 8B is an enlarged perspective view of the distal end portion of the apparatus of FIG. 8A;

FIG. 9A is a perspective view of the apparatus of FIG. 1 showing the outer rails in the fully deployed position, the inner rails in the fully deployed position, and the carriers extended over the inner rails to the fully deployed (advanced) position;

FIG. 9B is an enlarged perspective view of the distal end portion of the apparatus of FIG. 9A;

FIG. 10 is a longitudinal sectional view illustrating the interaction of the deployment rings, rails and carriers when the apparatus is in the initial position;

FIG. 11 is an enlarged view of a portion of the apparatus of FIG. 10 showing the proximal deployment rings for advancing the rails;

FIG. 12 is an enlarged view of a portion of the apparatus of FIG. 10 showing the distal deployment ring for advancing the carriers;

FIG. 13 is a longitudinal sectional view illustrating the interaction of the deployment rings, rails and carriers when the apparatus is in the fully deployed position;

FIG. 14 is an enlarged view of a portion of the apparatus of FIG. 13 showing the interaction of the deployment rings, rails and carriers;

FIG. 15 is an enlarged perspective view of the distal end of the apparatus of FIG. 13;

FIG. 16 is a further enlarged view of the distalmost portion of the apparatus of FIG. 15 illustrating the carriers fully advanced over the inner rails;

FIG. 17A is an enlarged transverse cross-sectional view showing engagement of the lock with the pin and carriers;

FIG. 17B is a further enlarged view of a portion of the apparatus shown in FIG. 17A;

FIG. 18A is an enlarged longitudinal sectional view showing the interaction of the pin, lock and rails in the deployed position of the apparatus;

FIG. 18B is an enlarged sectional view, cut in the longitudinal and transverse planes showing the interaction of the pin, lock and catheter in the deployed position of the apparatus;

FIG. 19 is an enlarged view of the apparatus of FIG. 1 showing a first embodiment of the carriers for supporting the cutting wire and suture;

FIG. 20 is an enlarged view of two of the carriers of FIG. 19 shown supporting the cutting wire and suture;

FIGS. 21A and 21B are enlarged front and rear views, respectively, of the carriers of FIG. 19 showing the cutting wire and suture extending through the respective openings;

FIG. 22 is an enlarged view of an alternate embodiment of the carrier having hooks to retain the cutting wire;

FIG. 24 is an enlarged view of the distal end of the apparatus of FIG. 23 showing the outer rails in the fully deployed position, the inner rails in the fully deployed position, and initial advancement of the carriers to advance the cutting wire, suture and tissue containment bag;

FIG. 25 is a top perspective view of the apparatus having an alternative mechanism for advancing the rails and carriers;

FIG. 26 is a bottom perspective view of the apparatus of FIG. 25;

FIGS. 27–34 are perspective views illustrating the method of using the apparatus of the present invention for excising breast tissue, wherein:

FIG. 27 illustrates the apparatus of the present invention approaching the breast to access the lesion;

FIG. 28 illustrates the cannula of the apparatus inserted through an incision in the breast in line with the lesion;

FIG. 29 illustrates the cannula inserted through an incision in the breast and the outer rails deployed proximally of the lesion;

FIG. 30 illustrates the inner rails deployed to an intermediate position and partially encircling the lesion;

FIG. 31 illustrates the inner rails fully deployed to encircle the lesion;

FIG. 32 illustrates partial deployment of the carriers to advance the cutting wire, suture and tissue retrieval bag;

FIG. 33 illustrates the carriers fully deployed with the tissue retrieval bag encircling the excised tissue;

FIG. 34 illustrates the apparatus with the tissue encapsulated in the retrieval bag withdrawn from the breast;

FIG. 35 is a perspective view of the apparatus inserted in a different orientation through an opening in a breast compression plate; and FIG. 36 is a perspective view of an alternate embodiment of the apparatus of the present invention having a transducer for imaging.

DETAILED DESCRIPTION OF PREFERRED EMBODIMENTS

Figure 23:
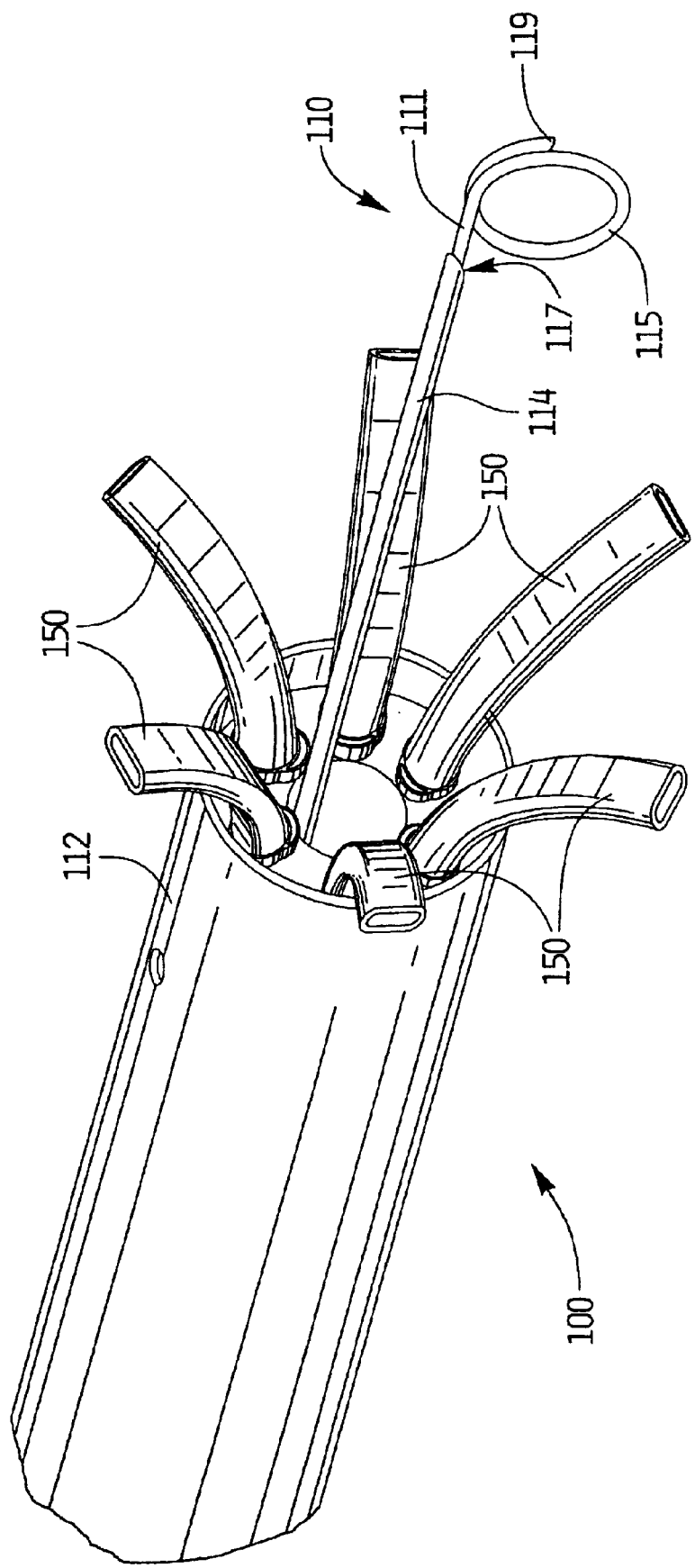
FIGS. 23 is a perspective view of an alternate embodiment of the apparatus of the present invention having a wire loop tissue marker, wherein the apparatus is shown with the marker deployed, the outer rails fully deployed, and the inner rails in the retracted position.

Referring now in detail to the drawings where like reference numerals identify similar or like components throughout the several views, the surgical apparatus for removing tissue is designated generally by reference numeral 10 in FIG. 1. The apparatus 10 of the present invention is particularly designed for removing breast tissue, however use of the apparatus for removal, i.e. biopsy, of other body tissue is contemplated.

Referring to FIGS. 1A and 2A, apparatus 10 has a housing or cannula 12, a series of deployment rings 20, 30, 40, and a handle portion 14. The ring 20 deploys outer (female) or first rails 50 and ring 30 deploys inner (male) or second rails 60. As shown, outer rails (or outer tissue penetrating members) 50 and second rails (or inner tissue penetrating members) 60 are deployed from an initial position retracted within lumen 18 of cannula 12 as shown in FIGS. 1A and 1B to a deployed position where outer rails 60 encircle the tissue to be biopsied. The tissue is then severed and removed in the manner described below. As will be appreciated, the apparatus 10 enables removal of a lesion through a relatively smaller incision since the cannula 12 determines the size of the entry incision to the target site, and the rails 60 deploy radially outwardly defining an area having a diameter larger than the diameter of the cannula, thereby allowing a larger area/volume of tissue to be removed.

Cannula or housing 12 can be composed of two separate cannulas: a proximal cannula 13 extending from conically shaped handle portion 14 and a reduced diameter cannula 16 extending distally from proximal cannula 13 and beginning at plastic interface 13a. Alternatively, cannula 12 can be composed of a single cannula having a larger diameter proximal portion (like cannula 13) and a smaller diameter distal portion (like cannula 16). A portion of cannula 16 or of the reduced diameter cannula portion is configured for insertion into the patient's body.

Cannula 13 preferably has a diameter D1 of about 13 mm and cannula 16 preferably has a diameter D2 of about 10 mm. Clearly other diameters are contemplated which can preferably range from about 30 mm to about 7 mm. Elongated slots 17a and 17b accommodate the respective pins of deployment rings 20, 30 and 40 in the manner described below. A pair of identical slots is formed on the opposite side of cannula 13 to accommodate the second pins of the deployment rings 20, 30 and 40.

As noted above, in the initial position, the outer rails 50 are fully retracted and housed within channel 18 of reduced diameter cannula 16 as shown in FIGS. 11A and 1B. Outer rails 50 have a central lumen 52 for telescopingly receiving inner rails 60. Thus, inner rails 60 are likewise retracted within cannula 16 in the initial position of the apparatus 10.

In this initial position shown in the sectional views of FIGS. 10–12, first and second proximal deployment rings 20 and 30 are in the proximalmost position adjacent handle portion 14 and distal deployment ring 40 is in its proximalmost position. A pair of pins 22, preferably spaced 180° apart, extends through respective apertures 24 in ring 20 to engage ring-like slug 25. Slug 25 has a pair of radial openings 21 to frictionally receive metal locks 23, and locks 23 have openings 26 to receive pins 22. In this manner, ring 20 is operatively attached to slug 25. The other radial openings 21, which although do not receive pins 22, have locks 23 seated therein.

Slug 25 also has a series of axial openings 28, corresponding in number to the number of outer rails 50, e.g. six. Outer rails 50 extend through these axial openings 28 in slug 25 and are affixed to locks 23. That is, locks 23 have a pair of spaced apart legs or tabs 29 (see also FIG. 18A) which frictionally engage notches at the proximal end of outer rails 50. In this manner, rails 50 are connected to slug 25 by frictional engagement with lock 23. Thus, when pins 22 (and ring 20) are slid forward in slot 17a, slug 25 and operatively connected outer rails 50 are advanced.

In a similar manner, ring 30 has a pair of pins 32 extending through respective apertures 34 to engage ring-like slug 35 and ring 40 has a pair of pins 42 extending through apertures 44 to engage ring-like slug 45. Slugs 35 and 45, like slug 25, frictionally receive locks 33, 43 within radial openings 36, 46, and have a series of axial openings 38, 48, to receive the inner rails 60 and carriers 70, respectively. The number of openings 38, 48 corresponds to the respective number of rails 60 and carriers 70. Locks 33 and 43 have openings 31, 41 to receive and secure the pins 32, 42. In this manner, rings 30 and 40 are operatively connected to slugs 35 and 45. Locks 33 and 43 also have tabs 39, 49 to receive the respective notches in the proximal portion of the rails 60 and carriers 70. Thus, rings 30, 40 are operatively connected to rails 60 and carriers 70, respectively, for deployment thereof. (Engagement of lock 43 with the notches 73 of carriers 70 is best seen in FIGS. 17B and 18B).

To deploy the outer rails 50, proximal deployment ring 20 is slid distally to advance slug 25, carrying the rails 50 distally to advance from channel 18 of cannula 16 to the deployed position as shown in FIGS. 3A and 3B. (The pins in these Figures as well as FIGS. 4–9 have been removed for convenience). Edge 19 of slot 17a functions as a positive stop to limit travel of proximal ring 20. As can be appreciated, in this position, rails 50 extend radially outwardly with respect to a longitudinal axis L of cannula 16. In this position, rails 50 can direct inner rails 60 upwardly and outwardly with respect to the reduced diameter cannula 16.

The outer rails 50 can have blunt tips as shown, or alternatively, to reduce the penetrating forces, can have more sharpened tips or beveled edges (described below) to facilitate cutting through tissue as they are advanced. Also, although six outer rails 50 are shown, a fewer or larger number of rails could be provided. Outer rails 50 are preferably composed of shape memory material with their memorized shape of that shown in FIG. 3B.

Once the outer rails 50 have been deployed, proximalmost deployment ring 30 is linearly advanced to advance the inner rails 60 from within lumen 52 of outer rails 50. As shown in FIGS. 4–5, as ring 34 is slid distally within elongated slot 17a of channel 12, slug 34 moves the inner rails 60 first radially outwardly with respect to the longitudinal axis L of cannula 16 at a similar angle to the angle of rails 50, and then in a direction somewhat parallel to the longitudinal axis L to begin encircling the target tissue (FIGS. 6A and 6B). Further advancement of ring 34 moves the inner rails 60 inwardly toward longitudinal axis (as extrapolated) with their tips 64 coming together as shown in FIGS. 2A and 2B. Deployment ring 20 can act as a stop for advancement of deployment ring 30. Alternatively, other means and mechanisms could be provided to provide a positive stop for advancement of the rings. In this fully advanced position, the rails 60 fully encapsulate, e.g., encircle the target tissue, defining a somewhat spherical tissue target region which can be of substantially circular or substantially elliptical transverse cross section. This target region has a diameter, defined by the distance D3 between the opposing inner rails 60, greater than diameter D2 of the distal cannula 16 and diameter D1 of proximal cannula 13, thus enabling a larger region of tissue to be removed than the diameter of the incision. In a preferred embodiment, the distance D3 is preferably slightly greater than about 3 cm, thereby allowing a 3 cm tissue region to be removed. It is also contemplated that other distances between the inner rails can be utilized.

As with the outer rails 50, inner rails 60 can have blunt tips as shown, or alternatively, to reduce the penetrating forces, can have sharper pointed tips or beveled edges to cut through tissue as they are advanced. FIGS. 30 and 32, discussed below, show by way of example beveled penetrating tips. Also, although six rails are shown, a fewer or larger number of rails could be provided. Inner rails 60 are preferably made of shape memory material which have a memorized shape of that shown in FIG. 2B.

As noted above, outer and inner rails 50, 60 are preferably made of shape memory metal material, such as Nitinol, a nickel titanium alloy. To facilitate passage of the outer rails 50 through the housing, e.g.; cannula 16, and facilitate passage of inner rails 60 through outer rails 50 into the tissue, cold saline is injected through or around the rails in their retracted position within cannula 16. This shape memory material characteristically exhibits rigidity in the austenitic state and more flexibility in the martensitic state. The cold saline maintains the temperature dependent rails 50, 60 in a relatively softer condition as they are in the martensitic state within the cannula. This facilitates the exit of outer rails 50 from cannula 16 and the exit of inner rails 60 from outer rails 50 as frictional contact between the tips of outer rails 50 and the inner surface of cannula 16 and frictional contact between the tips of inner rails 60 and the inner walls of outer rails 50 would otherwise occur if the rails were maintained in a rigid, i.e. austenitic, condition.

After deployment of the outer rails 50, they are exposed to the warmer body temperature. This change in temperature causes the rails 50 to transition to their austenitic state to facilitate passage through the tissue. Similarly, after deployment of inner rails 60 from outer rails 50, they are exposed to the warmer body temperature, thereby causing rails 60 to transition to their austenitic state to facilitate passage through tissue. A stopcock could be provided to ensure constant infusion of cold saline during advancement of the rails.

Once the inner rails 60 have been fully deployed, the carriers or catheters 70 are deployed to advance cutting wire 86 and suture 82 which is attached to tissue containment bag 84. (The cutting wire 86, suture 82 and bag 84 are not shown in FIGS. 7–9 for clarity). More specifically, as shown in FIGS. 7A and 7B, movement of distal ring 40 in a distal direction, advances carriers 70 from channel 18 of cannula 16 as pins 42 extending through distal ring 40 slide within slot 17b to advance slug 44.

One embodiment of the carriers 70 for retaining and advancing the wire 86 and suture 82 is shown in FIGS. 19–21. Each carrier 70 has a pair of cutting wire openings 74a, 74b and a pair of suture openings 72a, 72b positioned slightly proximally of openings 72a, 72b so that during advancement of carriers 70, suture 82 will trail cutting wire 86. One of the carriers 70 has a longitudinal slot 71 (see FIG. 18B) to enable the cutting wire 86 and suture 82 to extend proximally for attachment to a tension spring described in more detail below. For ease of manufacturing, each of the catheters 70 has a longitudinal slot so identical catheters can be made, however, optionally only one of the catheters 70 needs to be provided with the slot since the free end of the wire 86 and suture 82 can use a single passage proximally through the cannulas 13 and 16.

Suture 82, as shown, is threaded through adjacent carriers 70 as it extends through opening 72a and exits opening 72b in one carrier 70, then extends through opening 72a and out opening 72b in an adjacent carrier 70, and continues through openings 72a, 72b of adjacent carriers 70 until it extends through all the carriers 70. One end of the suture 82 is looped (reference numeral 83) around tissue containment bag 84 and attached thereto so that tensioning of the suture 82 cinches the open end of bag 84 to close the bag around the tissue severed by cutting wire 86. The free end of suture 82 extends rearwardly through (e.g. through slot 71) or adjacent one of the carriers 70, and extends proximally within with one end affixed to the cannula or handle. To enable tensioning of the suture 82, preferably a constant force spring (not shown) is mounted at one end within cannula 12 or handle 14. The free end of suture 82 is mounted to the other end of the spring so that advancement of the suture 82 by the carriers 70 unravels the spring and applies tension thereto, thereby applying tension to suture 82 to close the mouth of the tissue containment bag 84 as it is fully advanced.

The cutting wire 86 is threaded through openings 74a, 74b in adjacent carriers 70 in a similar manner as suture 82. That is, wire 86 extends into a carrier 70 through opening 74a and exits the carrier 70 through opening 74b where it can enter opening 74a in adjacent carrier 80. The wire is formed into a loop 85 as shown, with the free end extending proximally through one of the carriers 70, e.g. through longitudinal slot 71, terminating within cannula 12. A constant force spring (not shown) is mounted at one end within cannula 12 or handle 14 and at another end to the proximal end of cutting wire 86. A connection wire (not shown) electrically connects cutting wire 86 to an RF frequency source for applying RF energy to the cutting wire 86. As cutting wire 86 is advanced, it is held in tension by the spring.

An opening 87 in carrier 70 has an internal diameter dimensioned to receive an outer rail 50 and an inner rail 60. In this manner, carriers 70, when advanced, can ride over rails 50, 60 to advance the cutting wire 86, suture 82 and bag 84. Cutting wire 86 is preferably mounted to a radiofrequency energy source so RF energy is applied as wire 86 is advanced distally with respect to the rails 60 to progressively cut and cauterize the tissue.

Distal movement of ring 40 advances carriers 70 as they initially ride over the outer rails 50 as shown in FIGS. 7A and 7B, with opening 87 fitting over the outer surface of rails 50. Further distal movement of ring 40 advance carriers 70 over inner rails 60 (FIGS. 8A and 8B) until they reach their final deployed position of FIGS. 9A and 9B. In this position, distal ring 40 is at the distalmost end of slot 17b, with the edge 15 (see FIG. 1A) of the slots 17b acting as a positive stop for pins 42 to limit forward travel of the ring 40 and slug 45, and consequently limit travel of the carriers 70. In this final position of the apparatus shown in FIGS. 9A and 9B, also shown in the enlarged views of FIGS. 15 and 16, the inner rails 60 and outer rails 50 are fully contained within channel 72 of carrier 70. In this position, the cutting wire and the suture (with attached tissue containment bag) have traveled fully over the rails 50, 60 to the distal tips 64 of inner rails 60.

Note that as the carrier 70 is initially advanced over the rails, the diameter of the loop 85 of cutting wire 86 is enlarged since in this region outer rails 50 and inner rails 60 extend radially outwardly away from the longitudinal axis of the cannula 16. As the carrier 70 is further advanced to intermediate region 63 of inner rail 60, i.e. the region where the distance between opposing rails 60 peak and just before they begin their inward orientation towards the longitudinal axis of cannula 16, the loop 85 will widen to its largest diameter, substantially equal to the diameter D3 between opposing rails. This largest diameter of loop 85 defines the largest diameter of the tissue region being cut. As the wire 86 continues to advance past intermediate portion 63 of rails 60, the diameter of the loop 85 reduces as the inner rails 60 extend inwardly towards the longitudinal axis L of cannula 16 and the distance between opposing inner rails 60 decreases. The spring attached at the proximal end applies constant tension to the wire 86 to reduce its loop size.

The suture loop 83 of suture 82, which slightly trails wire 86, is expanded and reduced in a similar manner as wire loop 85 as the carriers 70 advance over the rails 50, 60. That is, suture loop 83 increases in diameter, to thereby widen the opening 88 in tissue containment bag 84, as carriers 70 advance to the intermediate region 63 of inner rails 60. After advance past the intermediate region 63, the suture loop 83 decreases in diameter to reduce the opening 88 in bag 84 as the spring at the proximal end of suture 82 applies constant tension to reduce the loop size. Thus, initial widening of suture loop 83 opens the mouth of bag 84 to receive the tissue mass severed by the cutting wire 86, and reduction of the loop 83 as the suture 84 is pulled proximally by the tension of the aforedescribed spring closes the mouth of the bag 84 to entrap the severed tissue. The severed tissue can then be removed, fully enclosed in the bag, to prevent any undesired leakage. The opening, i.e. expansion, of the cutting wire 86 and the bag 84 is also described below in conjunction with the method of FIGS. 27–34.

Note that carriers 70 can have blunt tips as shown, or alternatively, to reduce the penetrating forces, can have pointed tips or beveled edges to cut through tissue as they are advanced. The number of carriers 70 can also vary, but preferably will be the same number as the number of outer and inner rails utilized. The carriers with the openings for the suture and wire can be integral with the elongated hollow member that rides over the rails or, alternatively, can be a separate component attached to the elongated members. For example, in FIG. 21B, the carrier 70 includes elongated carrier pusher 77 which can be integral with or attached thereto.

It is also contemplated, that instead of being retained inside cannula 12, e.g. cannula 16, prior to deployment, the tissue retrieval bag could alternatively be mounted outside the cannula, e.g. outside cannula 16. This would reduce the overall size requirements of the cannula since the additional room for the folded bag within the cannula would not be required.

FIG. 22 illustrates an alternative embodiment of a carrier for retaining the cutting wire, suture and tissue retrieval bag. The bag and suture are mounted in a similar fashion as in the embodiment of FIGS. 21. However, instead of openings through the carrier 70, for the cutting wire, the carriers 70' each have an eyelet 75 to retain the wire. The eyelets 75 are formed at the end-of rods 76 which extending through longitudinal slot 71. The free end of the wire 86 would extend through one of the longitudinal slots 71 in carrier 70 to a proximally positioned spring. This embodiment allows the entire region of the wire to be exposed to tissue. The suture is not shown for clarity but would extend through openings in the carrier in the identical manner as FIG. 21.

In an alternate embodiment of FIGS. 23 and 24, a localization marker 110 can be utilized to identify the region and provide sonographic or x-ray visualization of the center of the tissue site. More specifically, apparatus 100 (only the distal portion is shown) contains a marker 110 having a wire 111 forming a wire loop 115, which is preferably made of shape memory material such as Nitinol. In the retracted position, support tube 114 is contained within the cannula 112 and loop 115 is contained within support tube 114 in a substantially straightened configuration substantially aligned with the longitudinal axis of the support tube 114 and the straight portions of wire 111. To mark the tissue site, support tube 114 is advanced from cannula 112, and then wire 111 is advanced from channel 117 of support tube 114 so that wire loop 115 extends distally therefrom. Once advanced from support tube 114, wire loop 115 returns to its memorized looped configuration of FIG. 23. A sharpened tip 119 facilitates insertion. Also, cold saline is injected into tube 114 as described above, thereby decreasing the frictional contact with the inner wall of tube 114 to facilitate advancement of the wire.

Wire loop 115 provides an indication via imaging or other visualization techniques of the target tissue, and more particularly a verification of the center of the target tissue. The rails 160 can then be advanced to encircle the wire marker 110 as shown in FIG. 24.

In all other respects, the apparatus 100 of FIGS. 23 and 24 is identical to apparatus 10 of FIGS. 1–22, as it includes outer rails 150, inner rails 160, carriers 170, a suture 182 attached to tissue containment bag 184, and a RF wire 186. The rails 150, 160 and carriers 170 are advanced in the same manner as in apparatus 10 and therefore are not described again.

It is also contemplated that the wire marker can be used as confirmation of the position of the deployed inner and outer rails 50 and 60. A lockout can be provided that would allow deployment of rails 50 and 60 only after the wire marker is advanced, thereby aiding the positioning of the rails with respect to the lesion.

Methods of utilizing the apparatus of the present invention for excising a lesion from the breast will now be described. It should be appreciated that the apparatus can be deployed either manually as in FIGS. 27–34, or machine actuated as in FIG. 35.

Turning first to the method illustrated in FIGS. 27–34, in this method, the breast is not compressed and the apparatus, designated generally by reference numeral 200, is deployed manually to access the target lesion and remove the lesion. Apparatus 200 is identical to apparatus 10 of FIGS. 1–21 except for the way the cutting wire is mounted to the carrier and the provision of beveled tips on the outer rails. The cutting wire is mounted to the apparatus via eyelets in the manner shown in FIG. 22. Consequently, the apparatus 200 has been labeled with reference numerals in the "200" series to correspond to the double digit reference numerals of apparatus 10. Mounting pins have also been removed for convenience.

Gripping handle portion 214, apparatus 200 is inserted through incision "i" in the breast to access tissue lesion "t". In this position, deployment rings 220, 230 and 240 are in their proximalmost positions in respective slots 217a, 217b with the outer (female) rails 250, inner (male) rails 260, and carriers (catheters) 270 retracted within reduced diameter cannula 16.

The cannula is then advanced through the incision "i" as shown in FIG. 28, in alignment with the lesion "t", with the rails 250, 260 and carriers 270 in the retracted position. Next, the outer rails 250 are advanced to the position of FIG. 29, still spaced proximally of lesion "t". Outer rails have a sharpened edge 251 to facilitate passage through tissue. The edge could alternately be beveled to facilitate passage.

Inner rails 260 are then advanced from within outer rails 250 to encircle the lesion "t" as shown in FIGS. 30 and 31. Note that inner rails have beveled tips 261 forming sharpened edges to facilitate passage through tissue. As appreciated, both outer rails 250 and inner rails 260 return to their memorized shape, corresponding to their positions in FIG. 31, as they exit from the cool saline within cannula 212 and are exposed to the warmer body temperature. Since the rails extend radially outwardly after insertion of the cannula, the diameter of the tissue region to be excised (which is preferably substantially circular in cross section) exceeds the diameter of the cannula. Stated another way, the size of the excised tissue region can be increased without requiring a corresponding increase in the size (outer diameter) of the cannula. The region encapsulated is substantially spherical in shape and is much larger than the lesion.

Next, as shown in FIGS. 32 and 33, carriers 270 are advanced to advance cutting wire 286 and suture 282 extending around the mouth of tissue containment bag 284. As cutting wire 286 is advanced by carrier 270 with respect to the outer rails 260, RF energy is applied to the wire 286 to cut and cauterize the tissue surround the lesion "t". As can be appreciated, the cutting wire 286 is progressively opened to a larger diameter as it is advanced to the intermediate region of the rails 260, substantially corresponding to the diameter of the sphere defined by the inner rails 260. This diameter is substantially larger than the diameter of the lesion "t" to be removed. Thus, not only is the entire lesion "t" removed, but also a safety margin of tissue, e.g., about 1 centimeter radially in all directions from the lesion, is excised. If the safety margin is about 1 centimeter radially, the area of tissue removed will be about 3 centimeters.

Trailing cutting wire 286 is suture 282 and tissue containment bag 284. Thus, suture 282 looped around the mouth of bag 284 progressively increases in diameter, thereby increasing the opening in the mouth of bag 284 as it is advanced to the intermediate region of outer rails 250. Thus, as lesion "t" is excised, it enters the mouth of bag 284 and is captured therein. As the bag 284 completes its travel, i.e.

the carrier 270 is advanced to the distal tips 261 of inner rails 260, the mouth of the bag 284 is automatically closed by the tension of suture 282 around the mouth of bag 284 due to the proximally applied force of the spring attached to the free end of the suture as described above. Thus the excised tissue is fully captured within bag 284. The lesion and area of surrounding tissue are withdrawn substantially intact for accurate pathology. Moreover, since sufficient margins have been removed, even if the tumor is malignant, a second surgery is not necessary. FIG. 34 illustrates apparatus 200 withdrawn from the breast with the tissue encapsulated within tissue containment bag 284. The rails 250 and 260 are elastically deformable to enable compression of the specimen as the apparatus is withdrawn through the relatively small incision.

FIG. 35 illustrates the use of the apparatus with machine controlled deployment. In the method of FIG. 35, the breast is compressed between compression plates P1 and P2 to facilitate imaging as well as access to the lesion "t." Apparatus 300 is advanced in the orientation shown, by table mounted controls (not shown), through aperture A in compression plate P2. That is, apparatus 300 would be positioned on a table, and advanced in a horizontal direction toward lesion "t". The inner and outer rails and carriers are then advanced by preset machine actuated controls which engage the deployment rings via pins (not shown) to excise and remove the lesion. This is achieved by mounting pins to the apertures 324, 334 and 344 in deployment rings 320, 330 and 340. The pins (not shown) will then be advanced by the table mounted actuators to advance the rings and connected slugs to deploy the rails and carriers in the manner described above.

The apparatus 400 of FIGS. 25 and 26 illustrates an example of machine controlled actuation similar to apparatus 300 of FIG. 35. This apparatus differs only in that it has sliders which optionally allow for manual advancement if desired. That is, instead of automated actuation, the surgeon can advance sliders 423, 433 and 443, which have internal pins connected to the slugs in the same manner as described above.

For machine actuation of apparatus 400, pins 422, 432 and 442 would be placed within slots in the machine, either in the orientation of FIG. 25 or the orientation of FIG. 26, depending on the orientation of the table mounted controls. The machine would be preset for controlled advancement of the pins, which would advance the rails and carriers in the same manner as pins 22, 32 and 42 of apparatus 10 described above. Optionally, an adapter can be mounted to the table which in turn mounts the apparatus.

In any of the foregoing embodiments of the biopsy apparatus of the present invention, the cannula can include a lumen for injection of drugs or agents to treat or destroy the target and/or surrounding tissue or to inhibit cell proliferation. The lumen can be a separate tube in the cannula, formed integral with the cannula or be the same lumen which contains the rails. Types of materials which can be injected include, for example, chemotherapeutic agents, cryogenic material, ablation fluid, heating fluid, etc. These materials can be delivered to the target region either before, after or during specimen removal.

IMAGING

FIG. 36 illustrates an embodiment of the apparatus which utilizes ultrasound to help guide and visualize the apparatus during insertion and use. Apparatus 500 is identical to apparatus 200 in all respects, except for the provision of ultrasonic transducer 501 (shown in phantom), and is therefore provided with corresponding reference numerals in the "500" series. Transducer 501 is positioned at the distal end of the apparatus 500, and is wired to a conventional power supply S. The wire extends inside cannula 512 and exits the proximal end of handle portion 514 as shown. Monitor screen M is wired to power supply S to enable viewing via ultrasound of the surgical site.

Currently, as is known, low ultrasound frequency provides increased ability to see a greater distance but at the expense of resolution. Conversely, high frequency provides greater (clearer) resolution but with a decreased ability to see distances. Thus, typically, since the ultrasound probe is placed outside the breast tissue, at a distance from the lesion, it must be used at a low frequency to ensure the lesion can be viewed. However, resolution suffers and difficulty in detecting the boundaries of the lesion could occur. Lower resolution also decreases the chances of detecting calcium which is often an indicator of the presence of abnormal growths, i.e. tumors. For this reason, the breast tissue is often compressed between compression plates to shorten the distance from the probe outside to the breast to the lesion. However, compression of the breast adds an additional step to the procedure and could distort the image and result in inaccurate lesion removal, especially if the lesion site is marked in a non-compressed condition of the breast.

In the apparatus 500, by placing the transducer at the end of the apparatus, the distance from the lesion is greatly reduced. This allows a higher frequency to be used which provides greater resolution and an increased ability to detect calcium. Also, by placement of the distal end of the instrument, the surgeon can view the lesion in an orientation aligned with the cannula, also facilitating vision.

It should be understood that the use of a transducer at the tip of the instrument can be used in other biopsy devices.

While the above description contains many specifics, those specifics should not be construed as limitations on the scope of the disclosure, but merely as exemplifications of preferred embodiments thereof. For example, the inner and outer rails can be reversed so that the set of rails which extends to encapsulate the lesion is positioned outside instead of inside, the initially deployed set of rails. Also, the cutting wire could be positioned outside rather than inside the rails. Additionally, although described for use for breast biopsy, the apparatus can be used to excise tissue in other areas of the body and in other surgical procedures. Those skilled in the art will envision many other possible variations that are within the scope and spirit of the disclosure as defined by the claims appended hereto.

What is claimed is:

1. A surgical biopsy apparatus comprising:

an elongated housing having a distal end portion and a proximal end portion;

at least three members each having a free end, the at least three members advanceable in a distal direction with the free end extending distally beyond the distal end portion of the housing to provide a three-dimensional boundary for an area of tissue to be removed, at least a portion of the at least three members extending in different directions;

a cutting wire loop advanceable distally with respect to the elongated housing from a proximal position to a more distal position to cut the area of tissue, wherein the cutting wire loop is moved to a larger diameter as it is advanced with respect to the elongated housing, and the cutting wire loop is supported by at least one carrier, the at least one carrier advanceable over one of at least three members.

2. The apparatus of claim 1, wherein the at least three members are composed of shape memory material.

3. The apparatus of claim 2, wherein exposure of the at least three members to body temperature transitions the members to an austenitic state.

4. A surgical biopsy apparatus comprising:

a housing having a longitudinal axis;

a plurality of tissue penetrating members extendable with respect to the housing at an angle to the longitudinal axis; and a carrier slidable with respect to and guided by the tissue penetrating members for advancing and expanding a wire to cut tissue, wherein the carrier has an opening to receive the wire therethrough.

5. The surgical biopsy apparatus of claim 4, further comprising a tissue containment bag, the tissue containment bag operatively associated with the carrier so that slidable movement of the carrier advances the tissue containment bag to the target tissue and expands an opening of the bag.

6. The apparatus of claim 4, further comprising a plurality of carriers, each carrier configured to slide over a respective tissue penetrating member.

7. The apparatus of claim 4, wherein the carrier has an additional opening for receiving a suture.

8. The apparatus of claim 7, wherein the suture is connected to a tissue retrieval bag for closing the bag.

9. The apparatus of claim 8, wherein the diameter of a loop of the suture increases as it is advanced distally with respect to the plurality of members.

10. A method for performing breast biopsy comprising:

inserting into breast tissue a housing having a diameter smaller than a diameter of the tissue to be biopsied;

advancing penetrating members through the breast tissue to create a tissue boundary area having a transverse cross-sectional length greater than the diameter of the housing; and advancing a cutting wire so a loop of the cutting wire moves to a diameter greater than the diameter of the housing as an opening of the loop expands in a plane substantially perpendicular to a longitudinal axis of the housing as the wire moves distally with respect to the penetrating members and is expanded by the penetrating members.

11. The method of claim 10, further comprising the step of advancing a tissue retrieval bag so the mouth of the bag moves to a diameter greater than the diameter of the housing as it is expanded by the penetrating members.

12. The method of claim 10, further comprising the step of passing radiofrequency through the cutting wire as it is advanced.

13. The method of claim 12, further comprising advancing a tissue containment bag to increase a transverse opening of a mouth of the bag in a plane substantially perpendicular to the longitudinal axis of the housing as the bag moves distally with respect to the penetrating members.

14. The method of claim 12, further comprising the step of advancing the cutting wire and tissue retrieval bag substantially simultaneously.

15. A surgical biopsy apparatus comprising:

a housing having a longitudinal axis;

a plurality of tissue penetrating members extendable with respect to the housing at an angle to the longitudinal axis; and a carrier slidable with respect to and guided by the tissue penetrating members for advancing and expanding a wire to cut tissue;

wherein the plurality of tissue penetrating members are extendable in a distal direction and the carrier slides in a distal direction so that the wire is expanded by the tissue penetrating members.

* * * * *